(12) United States Patent
Quddus et al.

(10) Patent No.: US 11,987,573 B2
(45) Date of Patent: May 21, 2024

(54) AMINOPYRIMIDINE/PYRAZINE DERIVATIVES AS CTPS1 INHIBITORS

(71) Applicant: Step Pharma S.A.S., Paris (FR)

(72) Inventors: Abdul Quddus, Nottingham (GB); Emma Blackham, Nottingham (GB)

(73) Assignee: Step Pharma S.A.S., Paris (FR)

( * ) Notice: Subject to any disclaimer, the term of this patent is extended or adjusted under 35 U.S.C. 154(b) by 581 days.

(21) Appl. No.: 17/287,137

(22) PCT Filed: Oct. 23, 2019

(86) PCT No.: PCT/EP2019/078848
§ 371 (c)(1),
(2) Date: Apr. 21, 2021

(87) PCT Pub. No.: WO2020/083975
PCT Pub. Date: Apr. 30, 2020

(65) Prior Publication Data
US 2021/0387965 A1 Dec. 16, 2021

(30) Foreign Application Priority Data

Oct. 23, 2018 (EP) ...................... 18202136
Dec. 21, 2018 (WO) ................ PCT/EP2018/086617
Mar. 22, 2019 (WO) ................ PCT/EP2019/057320

(51) Int. Cl.
C07D 401/14 (2006.01)
A61P 35/00 (2006.01)
C07D 405/14 (2006.01)

(52) U.S. Cl.
CPC ............ C07D 401/14 (2013.01); A61P 35/00 (2018.01); C07D 405/14 (2013.01)

(58) Field of Classification Search
CPC .. C07D 401/14; C07D 405/14; C07D 401/12; C07D 403/12; A61P 35/00
See application file for complete search history.

(56) References Cited

U.S. PATENT DOCUMENTS

| | | | |
|---|---|---|---|
| 2003/0158218 A1 | 8/2003 | Nantermet et al. | |
| 2008/0139557 A1 | 6/2008 | Blomgren et al. | |
| 2016/0152583 A1 | 6/2016 | Arisawa et al. | |
| 2021/0002269 A1 | 1/2021 | Quddus et al. | |
| 2021/0024507 A1 | 1/2021 | Quddus et al. | |
| 2021/0380575 A1 | 12/2021 | Novak et al. | |
| 2023/0192673 A1* | 6/2023 | Quddus ................ | C07D 401/14 514/210.18 |

FOREIGN PATENT DOCUMENTS

| | | |
|---|---|---|
| CN | 104262071 | 1/2015 |
| EP | 1659113 A1 | 5/2006 |
| EP | 2292603 A1 | 3/2011 |
| GB | 1555007 | 11/1979 |
| GB | 1575803 | 10/1980 |
| WO | 02/16318 A1 | 2/2002 |
| WO | 02/24665 A1 | 3/2002 |
| WO | 2006/010751 A1 | 2/2006 |
| WO | WO-2006050908 A1 * | 5/2006 ........... C07D 213/76 |
| WO | 2009/075874 A1 | 6/2009 |
| WO | 2014/090715 A1 | 6/2014 |
| WO | 2014/170435 A2 | 10/2014 |
| WO | 2015/094119 A1 | 6/2015 |
| WO | 2019/106146 A1 | 6/2019 |
| WO | 2019/106156 A1 | 6/2019 |
| WO | WO 2019/179652 A1 | 9/2019 |
| WO | WO 2022/087634 A1 | 4/2022 |

OTHER PUBLICATIONS

Walther, Raoul, et al. "Prodrugs in Medicinal Chemistry and Enzyme Prodrug Therapies." Advanced Drug Delivery Reviews, vol. 118, Sep. 2017, pp. 65-77. DOI.org (Crossref), https://doi.org/10.1016/j.addr.2017.06.013. (Year: 2017).*
U.S. Appl. No. 17/615,879, Quddus et al.
U.S. Appl. No. 17/615,873, Quddus et al.
U.S. Appl. No. 17/760,886, Novak et al.
U.S. Appl. No. 17/760,861, Novak et al.
Lynch et al., "Structural basis for isoform-specific inhibition of human CTPS1," PNAS, 118 (40): e2107968118 (2021).
Sakamoto et al., "Identification of cytidine-5-triphosphate synthase1-selective inhibitory peptide from random peptide library displayed on T7 phage," Peptides, 94: 56-63 (2017).
Ananthakrishnanadar et al., "The Effects of Substituents on the Rate of Saponification of Biphenyl-4-carboxylates," Journal of the Chemical Society, Perkin Transactions 2, 11 (1): 35-37 (1984).
Klapars et al., "Copper-Catalyzed Halogen Exchange in Aryl Halides: an Aromatic Finkelstein Reaction," Journal of the American Chemical Society, 124: 14844-14845 (2002).
McCluskey et al., "Exploring the Potent Inhibition of CTP Synthase by Gemcitabine-5'-Triphosphate," Chembiochem, 17: 2240-2249 (2016).
Meng et al., "Carboxylation of Aromatic and Aliphatic Bromides and Triflates with CO2 by Dual Visible-Light-Nickel Catalysis," Angewandt Chemie International Edition, 56: 13426-13430 (2017).
Zhao et al., "Design, synthesis and evaluation of aromatic heterocyclic derivatives as potent antifungal agents," European Journal of Medicinal Chemistry, 137: 96-107 (2017).

(Continued)

Primary Examiner — Clinton A Brooks
Assistant Examiner — Kyle Nottingham
(74) Attorney, Agent, or Firm — Morgan, Lewis & Bockius LLP

(57) ABSTRACT

Compounds of formula (I), and related aspects.

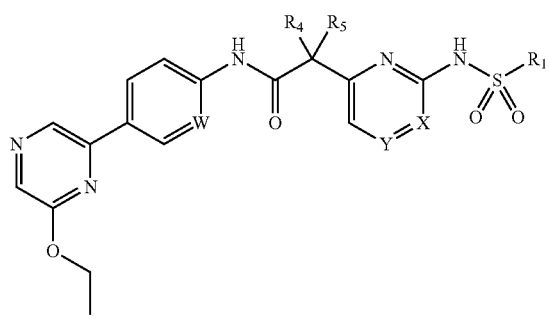

(I)

5 Claims, No Drawings

(56) References Cited

OTHER PUBLICATIONS

Lai et al., "A biocompatible inverse electron demand Diels-Alder reaction of aldehyde and tetrazine promoted by proline," New Journal of Chemistry, 40: 8194-8197 (2016).
Thirumoorthi et al., "A practical metal-free homolytic aromatic alkylation protocol for the synthesis of 3-(pyrazin-2-yl) bicyclo[1.1.1]pentane-1-carboxylic acid," Organic & Biomolecular Chemistry, 14: 9485-9489 (2016).
Wang et al., "Diamondoid-structured polymolybdate-based metal-organic frameworks as high-capacity anodes for lithium-ion batteries," ChemComm, 53: 5204-5207 (2017).
Sandosham et al., "Synthesis of Pyrimidinyl Triflates and Palladium-Catalyzed Coupling with Organotin and Organozinc Reagents," Heterocycles, 37 (1): 501-514 (1994).
Novak, et al., "Delivered and Optimization of Potent and Orally Available CTP Synthetase Inhibitors for Use in Treatment of Disease Driven by Aberrant Immune Cell Proliferation," Journal of Medicinal Chemistry, 2022, pubs.acs.org/jmc, 11 pages.
Schimmel, et al., "Cyclopentenyl Cytosine (CPEC): an Overview of its in vitro and in vivo Activity," Current Cancer Drug Targets, 2007, vol. 7, pp. 504-509.
Tang et al., "CTP synthase 1, a smooth muscle-sensitive therapeutic target for effective vascular repair", Atherosclerosis, Thrombosis and Vascular Biology, 2013, 33, 2336-2344.
Parker et al., "Inhibition of CTP Synthase 1 (CTPS1) is a Targeted Therapy for Metabolic Vulnerability in de novo Nucleotide Synthesis for Lymphomas and Leukemias", American Society of Hematology, 2021 (abstract and slides).
Asnagli et al., "Inhibition of CTP Synthase 1 (CTPS1) blocks T- and B-cell proliferation in vitro and the inflammatory response in vivo in a delayed-type hypersensitivity model", Autoimmunity Congress 2021 (abstract and slides).
Asnagli et al., "STP938, a novel, potent and selective inhibitor of CTP Synthase 1 (CTPS1) demonstrates efficacy in rodent models of inflammation and arthritis", European Alliance of Associations for Rheumatology 2021 (abstract and slides).
Pfeiffer et al., "Tackling pyrimidine biosynthesis—CTP Synthase 1 is a novel target in the treatment of multiple myeloma", International Myeloma Workshop 2021 (abstract and poster).
Chiron et al., "STP938, a selective CTPS1 inhibitor, shows single agent activity and synergy with BCL2 inhibition in preclinical models of mantle cell lymphoma", American Society for Hematology 2022 (abstract and poster).
Pfeiffer et al., "CTPS1 Is a Novel Therapeutic Target inMultiple Myeloma That Synergizes withInhibition of ATR, CHEK1 or WEE1", American Society for Hematology 2022 (abstract and poster).
Asnagli et al., "Selective Small Molecule Inhibition of CTP Synthase 1 (CTPS1) Suppresses T Cell Proliferation and Cytokine Release, Highlighting a Novel Therapeutic Target for Graft-Versus-Host Disease", European Hematology Association 2022 (abstract and poster).
Pfeiffer et al., "CTPS1 is a Novel Therapeutic Target in Myeloma—Selective Small Molecule Inhibition Delivers Single Agent Activity and Synergises With ATR Inhibition", European Hematology Association 2022 (abstract and poster).
Asnagli et al., "CTP Synthase 1 Is a Novel Target in T Cell Cancers, With Small Molecule Inhibition Inducing Death of Neoplastic Human T Cells In Vitro and Inhibition of Their Growth in an In Vivo Xenotransplant Model", European Hematology Association 2022 (abstract and poster).
Beer et al., "STP938, a clinic ready, first in class inhibitor of CTP Synthase 1 (CTPS1), demonstrates efficacy in preclinical models of human T cell neoplasia", T-cell Lymphoma forum 2022 (abstract, poster and slides).
Asnagli et al., "CTP Synthase 1 Is a Novel Therapeutic Target in Lymphoma", HemaSphere (2023) 7:4(e864). http://dx.doi.org/10.1097/HS9.0000000000000864.
Parker et al., "Combined CTPS1 + DDR pathway inhibition delivers synergistic anti-cancer activity", DDR Inhibitors Summit 2023 (poster).
Novak, "From hammer to scalpel: Honing a blunt instrument into a precision therapeutic", Acs San Francisco Poster 2023 (slides).
Minet et al., "Differential roles of CTP synthetases CTPS1 and CTPS2 in cell proliferation", Life Sciences Alliance 2023 vol. 6 | No. 9 | e202302066, https://doi.org/10.26508/1sa.202302066.
Pfeiffer et al., "CTPS1 is a novel therapeutic target in multiple myeloma which synergizes with inhibition of CHEK1, ATR or WEE1", Leukemia 2023 38181 192 https://doi.org/10.1038/s41375-023-02071-z.
Novak, "Discovery and Optimisation of Potent and Orally Available CTP Synthetase Inhibitors", 4th Alpine Winter Conference on Medicinal and Synthetic Chemistry 2024 (poster).

\* cited by examiner

AMINOPYRIMIDINE/PYRAZINE DERIVATIVES AS CTPS1 INHIBITORS

RELATED APPLICATIONS

This application is a U.S. National Phase Application under 35 U.S.C. § 371 of International Application No. PCT/EP2019/078848, filed October 23, 2019, which claims priority to, and the benefit of, European Application No. 18202136.0, filed Oct. 23, 2018, International Application No. PCT/EP2018/086617, filed Dec. 21, 2018, and International Application No. PCT/EP2019/057320, filed Mar. 22, 2019. The contents of each of these applications are incorporated herein by reference in their entirety.

FIELD OF THE INVENTION

The invention relates to novel compounds, processes for the manufacture of such compounds, related intermediates, compositions comprising such compounds and the use of such compounds as cytidine triphosphate synthase 1 inhibitors, particularly in the treatment or prophylaxis of disorders associated with cell proliferation.

BACKGROUND OF THE INVENTION

Nucleotides are a key building block for cellular metabolic processes such as deoxyribonucleic acid (DNA) and ribonucleic acid (RNA) synthesis. There are two classes of nucleotides, that contain either purine or pyrimidine bases, both of which are important for metabolic processes. Based on this, many therapies have been developed to target different aspects of nucleotide synthesis, with some inhibiting generation of purine nucleotides and some pyrimidine nucleotides or both.

The pyrimidine nucleotide cytidine 5' triphosphate (CTP) is a precursor required not just for the anabolism of DNA and RNA but also phospholipids and sialyation of proteins. CTP originates from two sources: a salvage pathway and a de novo synthesis pathway that depends on two enzymes, the CTP synthases (or synthetases) 1 and 2 (CTPS1 and CTPS2) (Evans and Guy 2004; Higgins, et al. 2007; Ostrander, et al. 1998).

CTPS1 and CTPS2 catalyse the conversion of uridine triphosphate (UTP) and glutamine into cytidine triphosphate (CTP) and L-glutamate:

The glutaminase domain generates ammonia from glutamine, via a covalent thioester intermediate with a conserved active site cysteine, generating glutamate. This ammonium is transferred from the glutaminase domain to the synthetase domain via a tunnel or can be derived from external ammonium. This ammonium is then used by the synthetase domain to generate CTP from the 4-phospho-UTP (Lieberman, 1956).

Although CTPS exists as two isozymes in humans and other eukaryotic organisms, CTPS1 and CTPS2, functional differences between the two isozymes are not yet fully elucidated (van Kuilenburg, et al. 2000).

The immune system provides protection from infections and has therefore evolved to rapidly respond to the wide variety of pathogens that the individual may be exposed to. This response can take many forms, but the expansion and differentiation of immune populations is a critical element and is hence closely linked to rapid cell proliferation. Within this, CTP synthase activity appears to play an important role in DNA synthesis and the rapid expansion of lymphocytes following activation (Fairbanks, et al. 1995; van den Berg, et al. 1995).

Strong clinical validation that CTPS1 is the critical enzyme in human lymphocyte proliferation came with the identification of a loss-of-function homozygous mutation (rs145092287) in this enzyme that causes a distinct and life-threatening immunodeficiency, characterized by an impaired capacity of activated T- and B-cells to proliferate in response to antigen receptor-mediated activation. Activated CTPS1-deficient cells were shown to have decreased levels of CTP. Normal T-cell proliferation was restored in CTPS1-deficient cells by expressing wild-type CTPS1 or by addition of cytidine. CTPS1 expression was found to be low in resting lymphocytes, but rapidly upregulated following activation of these cells. Expression of CTPS1 in other tissues was generally low. CTPS2 seems to be ubiquitously expressed in a range of cells and tissues but at low levels, and the failure of CTPS2, which is still intact in the patients, to compensate for the mutated CTPS1, supports CTPS1 being the critical enzyme for the immune populations affected in the patients (Martin, et al. 2014).

Overall, these findings suggest that CTPS1 is a critical enzyme necessary to meet the demands for the supply of CTP required by several important immune cell populations.

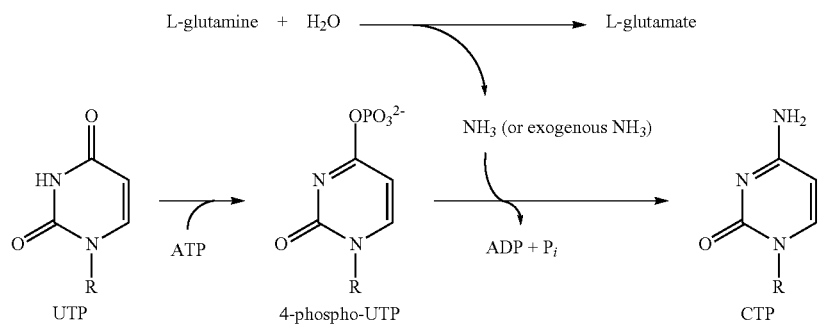

Both enzymes have two domains, an N-terminal synthetase domain and a C-terminal glutaminase domain (Kursula, et al. 2006). The synthetase domain transfers a phosphate from adenosine triphosphate (ATP) to the 4-position of UTP to create an activated intermediate, 4-phospho-UTP.

Normally the immune response is tightly regulated to ensure protection from infection, whilst controlling any response targeting host tissues. In certain situations, the control of this process is not effective, leading to immune-mediated pathology. A wide range of human diseases are thought to be due to such inappropriate responses mediated by different elements of the immune system.

Given the role that cell populations, such as T and B lymphocytes, are thought to play in a wide range of autoimmune and other diseases, CTPS1 represents a target for a new class of immunosuppressive agents. Inhibition of CTPS1 therefore provides a novel approach to the inhibition of activated lymphocytes and selected other immune cell populations such as Natural Killer cells, Mucosal-Associated Invariant T (MAIT) and Invariant Natural Killer T cells, highlighted by the phenotype of the human mutation patients (Martin, et al. 2014).

Cancer can affect multiple cell types and tissues but the underlying cause is a breakdown in the control of cell division. This process is highly complex, requiring careful coordination of multiple pathways, many of which remain to be fully characterised. Cell division requires the effective replication of the cell's DNA and other constituents. Interfering with a cell's ability to replicate by targeting nucleic acid synthesis has been a core approach in cancer therapy for many years. Examples of therapies acting in this way are 6-thioguanine, 6-mecaptopurine, 5-fluorouracil, cytarabine, gemcitabine and pemetrexed.

As indicated above, pathways involved in providing the key building blocks for nucleic acid replication are the purine and pyrimidine synthesis pathways, and pyrimidine biosynthesis has been observed to be up-regulated in tumors and neoplastic cells.

CTPS activity is upregulated in a range of tumour types of both haematological and non-haematological origin, although heterogeneity is observed among patients. Linkages have also been made between high enzyme levels and resistance to chemotherapeutic agents.

Currently, the precise role that CTPS1 and CTPS2 may play in cancer is not completely clear. Several non-selective CTPS inhibitors have been developed for oncology indications up to phase I/II clinical trials, but were stopped due to toxicity and efficacy issues.

Most of the developed inhibitors are nucleoside-analogue prodrugs (3-deazauridine, CPEC, carbodine), which are converted to the active triphosphorylated metabolite by the kinases involved in pyrimidine biosynthesis: uridine/cytidine kinase, nucleoside monophosphate-kinase (NMP-kinase) and nucleoside diphosphatekinase (NDP-kinase). The remaining inhibitors (acivicin, DON) are reactive analogues of glutamine, which irreversibly inhibit the glutaminase domain of CTPS. Gemcitibine is also reported to have some inhibitory activity against CTPS (McClusky et al., 2016).

CTPS therefore appears to be an important target in the cancer field. The nature of all of the above compounds is such that effects on other pathways are likely to contribute to the efficacy they show in inhibiting tumours.

Selective CTPS inhibitors therefore offer an attractive alternative approach for the treatment of tumours. Compounds with different potencies against CTPS1 and CTPS2 may offer important opportunities to target different tumours depending upon their relative dependence on these enzymes.

CTPS1 has also been suggested to play a role in vascular smooth muscle cell proliferation following vascular injury or surgery (Tang, et al. 2013).

As far as is known to date, no selective CTPS1 inhibitors have been developed. Recently, the CTPS1 selective inhibitory peptide CTpep-3 has been identified. The inhibitory effects of CTpep-3 however, were seen in cell free assays but not in the cellular context. This was not unexpected though, since the peptide is unlikely to enter the cell and hence is not easily developable as a therapeutic (Sakamoto, et al. 2017).

In summary, the available information and data strongly suggest that inhibitors of CTPS1 will reduce the proliferation of a number of immune and cancer cell populations, with the potential for an effect on other selected cell types such as vascular smooth muscle cells as well. Inhibitors of CTPS1 may therefore be expected to have utility for treatment or prophylaxis in a wide range of indications where the pathology is driven by these populations.

CTPS1 inhibitors represent a novel approach for inhibiting selected components of the immune system in various tissues, and the related pathologies or pathological conditions such as, in general terms, rejection of transplanted cells and tissues, Graft-related diseases or disorders, allergies and autoimmune diseases. In addition, CTPS1 inhibitors offer therapeutic potential in a range of cancer indications and in enhancing recovery from vascular injury or surgery and reducing morbidity and mortality associated with neointima and restenosis.

International patent applications WO2019/106156, WO2019/106146, WO2019/179652 and WO2019/180244 disclose CTPS1 inhibitors.

There is a need for further CTPS1 inhibitors which may demonstrate beneficial properties such as:

high potency;

selective inhibition of CTPS1 over CTPS2;

good cellular permeability;

high free fraction;

desirable pharmacodynamic and pharmacokinetic parameters;

distinct metabolites;

low to moderate lipophilicity.

SUMMARY OF THE INVENTION

The invention provides a compound of formula (I):

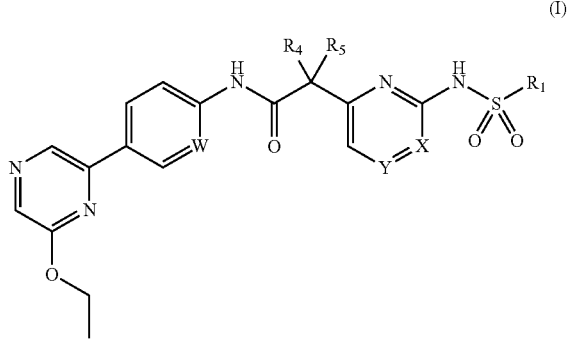

(I)

wherein:
(a) when $R_4$, $R_5$, X, Y and $R_1$ are as follows:

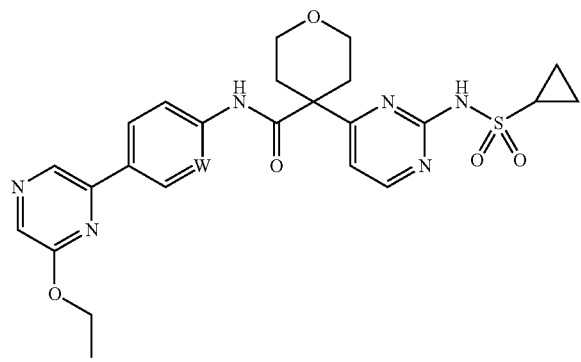

then W is N, CH or CF;
(b) when $R_4$, $R_5$, X, W and $R_1$ are as follows:

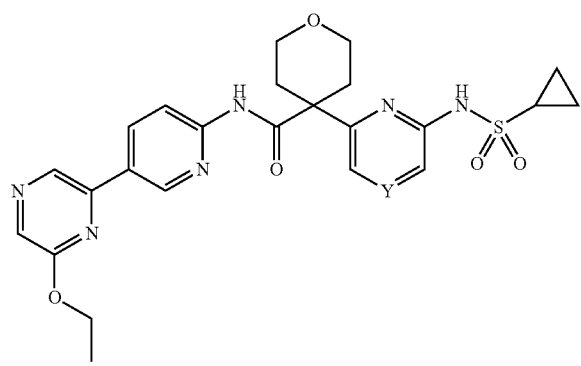

then Y is CH or N;
(c) when W, X, Y and $R_1$ are as follows:

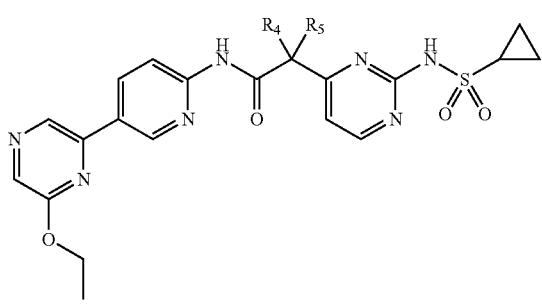

then $R_4$ and $R_5$ are joined to form the following structures:

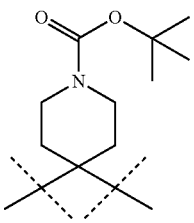 or 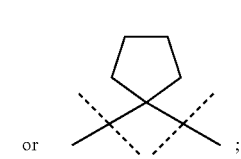 ;

(d) when W, $R_4$, $R_5$, X and Y are as follows:

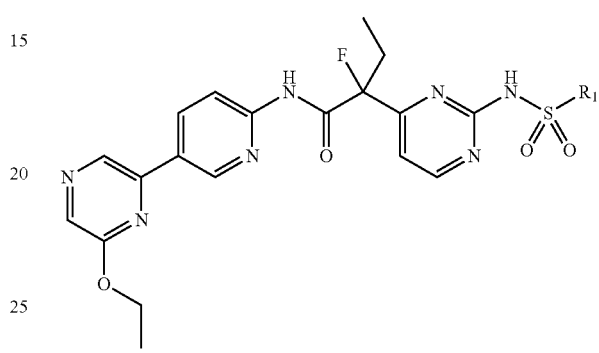

then $R_1$ is methyl or cyclopropyl; and
(e) the compound is selected from the group consisting of:

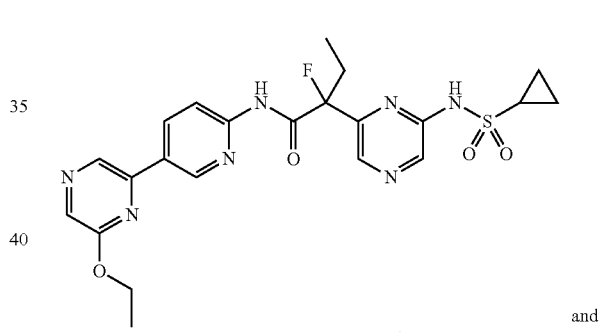

and

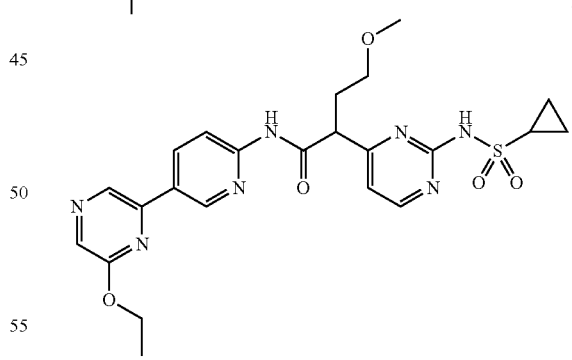

A compound of formula (I) may be provided in the form of a salt and/or solvate thereof and/or derivative thereof. Suitably, the compound of formula (I) may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Also provided is a compound of formula (I), or a pharmaceutically acceptable salt and/or solvate thereof and/or derivative thereof, for use as a medicament, in particular for use in the inhibition of CTPS1 in a subject or the prophylaxis or treatment of associated diseases or disorders, such as those in which a reduction in T-cell and/or B-cell proliferation would be beneficial.

Further, there is provided a method for the inhibition of CTPS1 in a subject or the prophylaxis or treatment of associated diseases or disorders, such as those in which a reduction in T-cell and/or B-cell proliferation would be beneficial, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the inhibition of CTPS1 in a subject or the prophylaxis or treatment of associated diseases or disorders, such as those in which a reduction in T-cell and/or B-cell proliferation would be beneficial.

Suitably the disease or disorder is selected from: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; and transplantation. In addition, the disease or disorder may be selected from myasthenia gravis, multiple sclerosis, and scleroderma/systemic sclerosis.

Also provided is a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Also provided is a compound of formula (I), or a pharmaceutically acceptable salt and/or solvate thereof and/or derivative thereof, for use in enhancing recovery from vascular injury or surgery and reducing morbidity and mortality associated with neointima and restenosis in a subject.

Further, there is provided a method for enhancing recovery from vascular injury or surgery and reducing morbidity and mortality associated with neointima and restenosis in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for enhancing recovery from vascular injury or surgery and reducing morbidity and mortality associated with neointima and restenosis in a subject.

Also provided are pharmaceutical compositions containing a compound of formula (I), or a pharmaceutically acceptable salt and/or solvate thereof and/or derivative thereof, and a pharmaceutically acceptable carrier or excipient.

Also provided are processes for preparing compounds of formula (I) and novel intermediates of use in the preparation of compounds of formula (I).

DETAILED DESCRIPTION OF THE INVENTION

The invention provides a compound of formula (I):

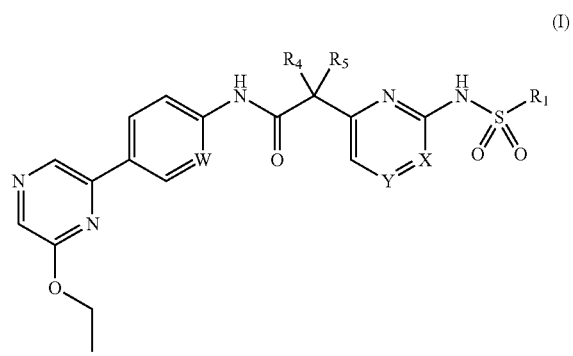

wherein:

(a) when $R_4$, $R_5$, X, Y and $R_1$ are as follows:

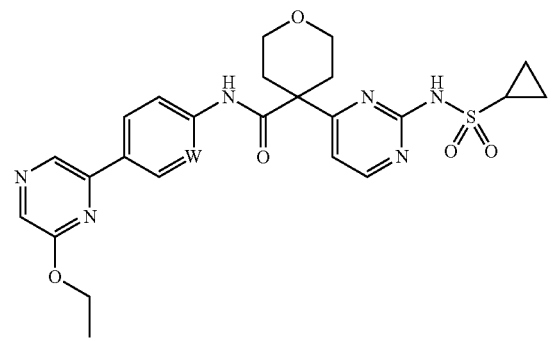

then W is N, CH or CF;

(b) when $R_4$, $R_5$, X, W and $R_1$ are as follows:

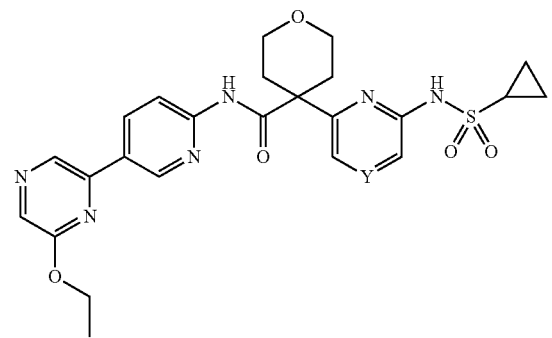

then Y is CH or N;

(c) when W, X, Y and R₁ are as follows:

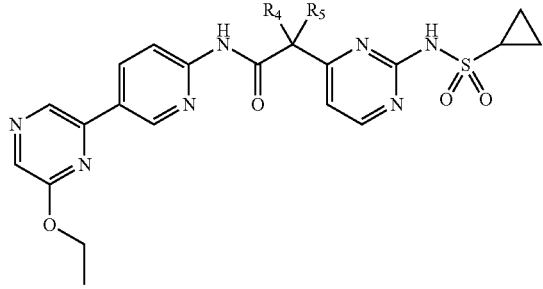

then R₄ and R₅ are joined to form the following structures:

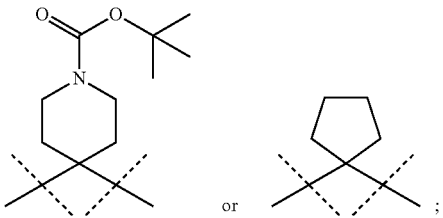

(d) when W, R₄, R₅, X and Y are as follows:

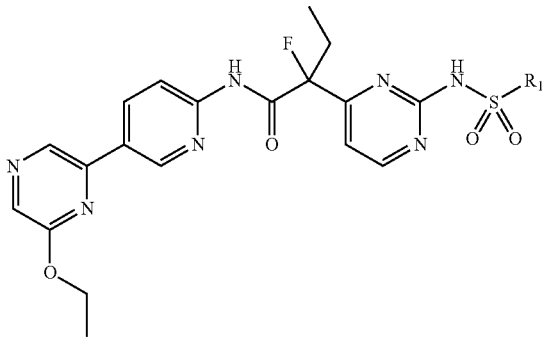

then R₁ is methyl or cyclopropyl; and (e) the compound is selected from the group consisting of:

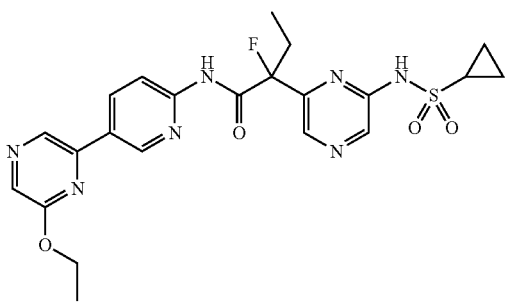

and

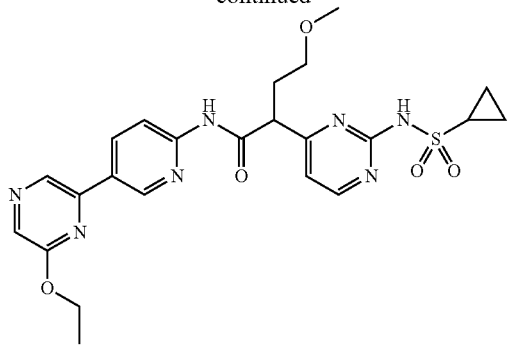

or a salt and/or solvate thereof and/or derivative thereof.
Suitably R₄ and R₅ are arranged in the following configuration:

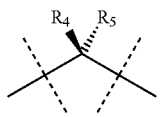

Alternatively, R₄ and R₅ are arranged in the following configuration:

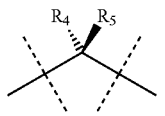

The present invention provides the following compounds:
(R)-2-(2-(cyclopropanesulfonamido)pyrimidin-4-yl)-N-(5-(6-ethoxypyrazin-2-yl)pyridin-2-yl)-2-fluorobutanamide;
(S)-2-(2-(cyclopropanesulfonamido)pyrimidin-4-yl)-N-(5-(6-ethoxypyrazin-2-yl)pyridin-2-yl)-2-fluorobutanamide;
4-(2-(cyclopropanesulfonamido)pyrimidin-4-yl)-N-(5-(6-ethoxypyrazin-2-yl)pyridin-2-yl)tetrahydro-2H-pyran-4-carboxamide;
1-(2-(cyclopropanesulfonamido)pyrimidin-4-yl)-N-(5-(6-ethoxypyrazin-2-yl)pyridin-2-yl)cyclopentane-1-carboxamide;
4-(2-(cyclopropanesulfonamido)pyrimidin-4-yl)-N-(4-(6-ethoxypyrazin-2-yl)phenyl)tetrahydro-2H-pyran-4-carboxamide;
tert-butyl 4-(2-(cyclopropanesulfonamido)pyrimidin-4-yl)-4-((5-(6-ethoxypyrazin-2-yl)pyridin-2-yl)carbamoyl)piperidine-1-carboxylate;
4-(2-(cyclopropanesulfonamido)pyrimidin-4-yl)-N-(4-(6-ethoxypyrazin-2-yl)-2-fluorophenyl)tetrahydro-2H-pyran-4-carboxamide;
2-(2-(cyclopropanesulfonamido)pyrimidin-4-yl)-N-(5-(6-ethoxypyrazin-2-yl)pyridin-2-yl)-4-methoxybutanamide;
(R)—N-(5-(6-ethoxypyrazin-2-yl)pyridin-2-yl)-2-fluoro-2-(2-(methylsulfonamido)pyrimidin-4-yl)butanamide;
(S)—N-(5-(6-ethoxypyrazin-2-yl)pyridin-2-yl)-2-fluoro-2-(2-(methylsulfonamido)pyrimidin-4-yl)butanamide;
4-(6-(cyclopropanesulfonamido)pyridin-2-yl)-N-(5-(6-ethoxypyrazin-2-yl)pyridin-2-yl)tetrahydro-2H-pyran-4-carboxamide;
4-(6-(cyclopropanesulfonamido)pyrazin-2-yl)-N-(5-(6-ethoxypyrazin-2-yl)pyridin-2-yl)tetrahydro-2H-pyran-4-carboxamide;

(R)-2-(6-(cyclopropanesulfonamido)pyrazin-2-yl)-N-(5-(6-ethoxypyrazin-2-yl)pyridin-2-yl)-2-fluorobutanamide; and (S)-2-(6-(cyclopropanesulfonamido)pyrazin-2-yl)-N-(5-(6-ethoxypyrazin-2-yl)pyridin-2-yl)-2-fluorobutanamide.

The compounds of the invention may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Compounds of the invention of particular interest are those demonstrating an $IC_{50}$ of 1 uM or lower, especially 100 nM or lower, in respect of CTPS1 enzyme, using the methods of the examples (or comparable methods).

Compounds of the invention of particular interest are those demonstrating a selectivity for CTPS1 over CTPS2 of 2-30 fold, suitably >30-60 fold or more suitably >60 fold, using the methods of the examples (or comparable methods). Desirably the selectivity is for human CTPS1 over human CTPS2.

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid or base addition salts with one or more equivalents of the acid or base. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^{2}$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Unnatural variant isotopic forms which incorporate deuterium i.e. 2H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^{2}$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth in the Examples, and modifications thereof.

Intermediates of the Invention

The present invention also relates to novel intermediates in the synthesis of compounds of formula (I) such as compounds of formula (II), (XXIV), (XXXI), (LVIII) and (IIa) wherein the variable groups and associated preferences are as defined previously for compounds of formula (I):

a compound of formula (II):

(II)

wherein R is H, $C_{1-6}$alkyl (e.g. methyl and ethyl) or benzyl;

a compound of formula (XXIV):

(XXIV)

wherein P is a nitrogen protecting group such as para-methoxybenzyl;

a compound of formula (XXXI):

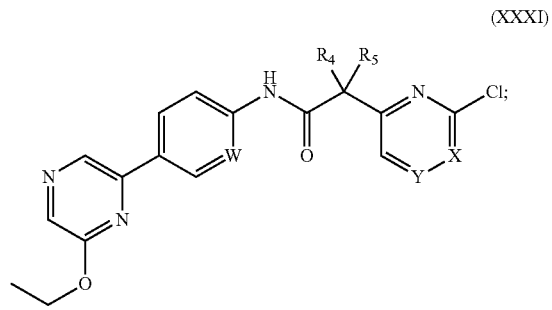

(XXXI)

a compound of formula (LVIII):

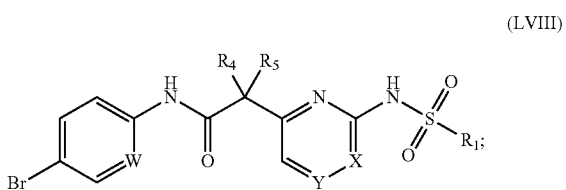

(LVIII)

a compound of formula (IIa):

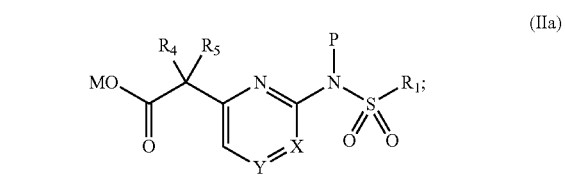

(IIa)

wherein P is a nitrogen protecting group such as para-methoxybenzyl and M is a metal ion such as $Li^+$.

Included as an aspect of the invention are all novel intermediates described in the examples, including those intermediates numbered INTC1 to INTC179.

Included as an aspect of the invention are salts such as pharmaceutically acceptable salts of any one of the intermediates disclosed herein, such as any one of compounds of formulae (II), (XXIV), (XXXI), (LVIII) and (IIa).

The compound of formula (LVIII) may be coupled under Suzuki conditions with a boronate ester of general formula (XII) as shown in Scheme 1. The boronate is usually a dihydroxyboryl or dialkyloxyboryl group, usually a 4,4,5,5-tetramethyl-1,3,3,2-dioxaborolan-2-yl group. The couplings according to the Suzuki method are performed, for example, by heating in the presence of a catalyst such as [1,1'-bis(diphenylphosphino)ferrocene]dichloropalladium (II) and an inorganic base such as potassium carbonate in a solvent mixture of dioxane and water. It will be understood by persons skilled in the art that many catalysts and conditions can be employed for such couplings.

Scheme 1

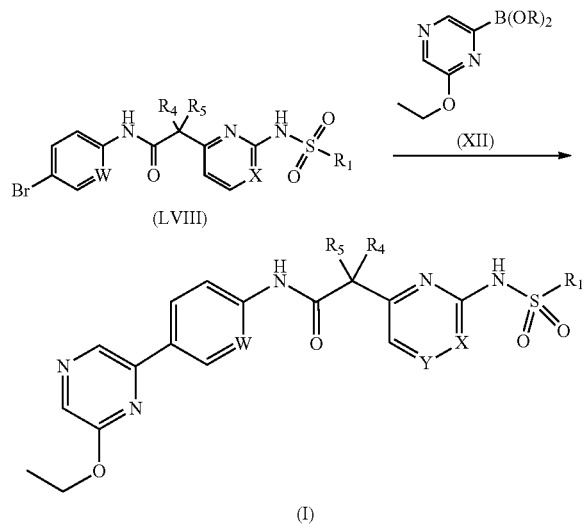

Therapeutic Methods

Compounds of formula (I) of the present invention have utility as inhibitors of CTPS1. Therefore, the invention also provides a compound of formula (I), or a pharmaceutically acceptable salt and/or solvate (e.g. salt) and/or derivative thereof, for use as a medicament, in particular in the treatment or prophylaxis of a disease or disorder wherein an inhibitor of CTPS1 is beneficial, for example those diseases and disorders mentioned herein below.

The invention provides a method for the treatment or prophylaxis of a disease or disorder wherein an inhibitor of CTPS1 is beneficial, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder wherein an inhibitor of CTPS1 is beneficial, for example those diseases and disorders mentioned herein below.

More suitably, the disease or disorder wherein an inhibitor of CTPS1 is beneficial is a disease or disorder wherein a reduction in T-cell and/or B-cell proliferation would be beneficial.

The invention also provides a compound of formula (I), or a pharmaceutically acceptable salt and/or solvate (e.g. salt) and/or derivative thereof, for use in the inhibition of CTPS1 in a subject.

The invention provides a method for the inhibition of CTPS1 in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the inhibition of CTPS1 in a subject.

The invention also provides a compound of formula (I), or a pharmaceutically acceptable salt and/or solvate (e.g. salt) and/or derivative thereof, for use in the reduction of T-cell and/or B-cell proliferation in a subject.

The invention provides a method for the reduction of T-cell and/or B-cell proliferation in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the reduction of T-cell and/or B-cell proliferation in a subject.

More suitably, the disease or disorder wherein an inhibitor of CTPS1 is beneficial is a disease or disorder wherein a reduction in T-cell and/or B-cell proliferation would be beneficial.

The term 'treatment' or 'treating' as used herein includes the control, mitigation, reduction, or modulation of the disease state or its symptoms.

The term 'prophylaxis' or 'preventing' is used herein to mean preventing symptoms of a disease or disorder in a subject or preventing recurrence of symptoms of a disease or disorder in an afflicted subject and is not limited to complete prevention of an affliction.

Suitably, the disease or disorder is selected from rejection of transplanted cells and tissues, Graft-related diseases or disorders, allergies and autoimmune diseases.

In one embodiment the disease or disorder is the rejection of transplanted cells and tissues. The subject may have been transplanted with a graft selected from the group consisting of heart, kidney, lung, liver, pancreas, pancreatic islets, brain tissue, stomach, large intestine, small intestine, cornea, skin, trachea, bone, bone marrow (or any other source of hematopoietic precursor cells and stem cells including hematopoietic cells mobilized from bone marrow into peripheral blood or umbilical cord blood cells), muscle, or bladder. The compounds of the invention may be of use in preventing or suppressing an immune response associated with rejection of a donor tissue, cell, graft or organ transplant in a subject.

In a further embodiment the disease or disorder is a Graft-related disease or disorder. Graft-related diseases or disorders include graft versus host disease (GVHD), such as GVHD associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc, and Host-Versus-Graft-Disease (HVGD). The compounds of the invention may be of use in preventing or suppressing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). Thus the compounds of the invention have utility in preventing Host-Versus-Graft-Disease (HVGD) and Graft-Versus-Host-Disease (GVHD).

A CTPS1 inhibitor may be administered to the subject before, after transplantation and/or during transplantation. In some embodiments, the CTPS1 inhibitor may be administered to the subject on a periodic basis before and/or after transplantation.

In another embodiment, the disease or disorder is an allergy.

In additional embodiments the immune related disease or disorder is an autoimmune disease. As used herein, an "autoimmune disease" is a disease or disorder directed at a subject's own tissues. Examples of autoimmune diseases include, but are not limited to Addison's Disease, Adult-onset Still's disease, Alopecia Areata, Alzheimer's disease, Anti-neutrophil Cytoplasmic Antibodies (ANCA)-Associated Vasculitis, Ankylosing Spondylitis, Anti-phospholipid Syndrome (Hughes' Syndrome), Aplastic Anemia, Arthritis, Asthma, Atherosclerosis, Atherosclerotic plaque, Atopic Dermatitis, Autoimmune Hemolytic Anemia, Autoimmune Hepatitis, Autoimmune Hypophysitis (Lymphocytic Hypophysitis), Autoimmune Inner Ear Disease, Autoimmune Lymphoproliferative Syndrome, Autoimmune Myocarditis, Autoimmune Neutropenia, Autoimmune Oophoritis, Autoimmune Orchitis, Auto-Inflammatory Diseases requiring an immunosuppressive treatment, Azoospermia, Bechet's Disease, Berger's Disease, Bullous Pemphigoid, Cardiomyopathy, Cardiovascular disease, Celiac disease including Refractory Celiac Disease (type I and type II), Chronic Fatigue Immune Dysfunction Syndrome (CFIDS), Chronic Idiopathic Polyneuritis, Chronic Inflammatory Demyelinating Polyneuropathy (CIPD), Chronic Relapsing Polyneuropathy (Guillain-Barre syndrome), Churg-Strauss Syndrome (CSS), Cicatricial Pemphigoid, Cold Agglutinin Disease (CAD), chronic obstructive pulmonary disease (COPD), CREST Syndrome, Cryoglobulin Syndromes, Cutaneous Lupus, Dermatitis Herpetiformis, Dermatomyositis, Eczema, Epidermolysis Bullosa Acquisita, Essential Mixed Cryoglubinemia, Evan's Syndrome, Exophthalmos, Fibromyalgia, Goodpasture's Syndrome, Grave's disease, Hemophagocytic Lymphohistiocytosis (HLH) (including Type 1 Hemophagocytic Lymphohistiocytosis), Histiocytosis/Histiocytic Disorders, Hashimoto's Thyroiditis, Idiopathic Pulmonary Fibrosis, Idiopathic Thrombocytopenia Purpura (ITP), IgA Nephropathy, Immunoproliferative Diseases or Disorders, Inflammatory Bowel Disease (IBD), Interstitial Lung Disease, Juvenile Arthritis, Juvenile Idiopathic Arthritis (JIA), Kawasaki's Disease, Lambert-Eaton Myasthenic Syndrome, Lichen Planus, Localized Scleroderma, Lupus Nephritis, Menibre's Disease, Microangiopathic Hemoytic Anemia, Microscopic Polyangitis, Miller Fischer Syndrome/Acute Disseminated Encephalomyeloradiculopathy, Mixed Connective Tissue Disease, Multiple Sclerosis (MS), Muscular Rheumatism, Myalgic Encephalomyelitis (ME), Myasthenia Gravis, Ocular Inflammation, Pemphigus Foliaceus, Pemphigus Vulgaris, Pernicious Anemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune Cholangiopathy, Primary Glomerulonephritis, Primary Sclerosing Cholangitis, Psoriasis, Psoriatic Arthritis, Pure Red Cell Anemia, Raynaud's Phenomenon, Reiter's Syndrome/Reactive Arthritis, Relapsing Polychondritis, Restenosis, Rheumatic Fever, Rheumatic Disease, Rheumatoid Arthritis, Sarcoidosis, Schmidt's Syndrome, Scleroderma/Systemic Sclerosis, Sjörgen's Syndrome, Stiff-Man Syndrome, The Sweet Syndrome (Febrile Neutrophilic Dermatosis), Systemic Lupus Erythematosus (SLE), Systemic Scleroderma, Takayasu Arteritis, Temporal Arteritis/Giant Cell Arteritis, Thyroiditis, Type 1 diabetes, Type 2 diabetes, Uveitis, Vasculitis, Vitiligo, Wegener's Granulomatosis, and X-linked lymphoproliferative disease.

Of particular interest are diseases and disorders which are mainly driven by T-cell activation and proliferation, including:
  diseases and disorders which are not linked to alloreactivity including:
    Alopecia areata, atopic dermatitis, eczema, psoriasis, lichen planus, psoriatic arthritis, vitiligo;
    Uveitis;
    Ankylosing spondylitis, Reiter's syndrome/reactive arthritis;
    Aplastic anemia, autoimmune lymphoproliferative syndrome/disorders, hemophagocytic lymphohistiocytosis;
    Type 1 diabetes; and
    Refractory celiac disease;
  Acute rejection of grafted tissues and transplanted organs; acute graft versus host disease (GVHD) after transplantation of bone marrow cells or any other source of allogenic cells including hematopoietic precursors cells and/or stem cells.

Also of interest are diseases and disorders which are driven by both T- and B-cell activation and proliferation, with an important involvement of B-cells, including:
  diseases and disorders for which the involvement of pathogenic auto-antibodies is well characterized, including:
    Allergy;
    Cicatricial pemphigoid, bullous pemphigoid, epidermolysis bullosa acquisita, pemphigus foliaceus, pemphigus vulgaris, dermatitis herpetiformis;
    ANCA-associated vasculitis and microscopic polyangitis, vasculitis, Wegener's granulomatosis; Churg-Strauss syndrome (CSS), polyarteritis nodosa, cryoglobulin syndromes and essential mixed cryglobulinemia;
    Systemic lupus erythematosus (SLE), antiphospholipid syndrome (Hughes' syndrome), cutaneous lupus, lupus nephritis, mixed connective tissue disease;
    Thyroiditis, Hashimoto thyroiditis, Grave's disease, exophthalmos;
    Autoimmune hemolytic anemia, autoimmune neutropenia, ITP, pernicious anaemia, pure red cell anaemia, micro-angiopathic hemolytic anemia;
    Primary glomerulonephritis, Berger's disease, Goodpasture's syndrome, IgA nephropathy; and
    Chronic idiopathic polyneuritis, chronic inflammatory demyelinating polyneuropathy (CIPD), chronic relapsing polyneuropathy (Guillain-Barre syndrome), Miller Fischer syndrome, Stiff man syndrome, Lambert-Eaton myasthenic syndrome, myasthenia gravis.
  diseases and disorders for which the involvement of B-cells is less clearly characterized (although sometimes illustrated by the efficacy of anti-CD20 monoclonal antibodies or intravenous immunoglobulin infusions) and may not correspond or be limited to the production of pathogenic antibodies (nevertheless, non-pathogenic antibodies are sometimes described or even often present and used as a diagnosis biomarker), including:
    Addison's disease, autoimmune oophoritis and azoospermia, polyglandular syndromes (Whitaker's syndrome), Schmidt's syndrome;
    Autoimmune myocarditis, cardiomyopathy, Kawasaki's disease;

Rheumatoid arthritis, Sjögren's syndrome, mixed connective tissue disease, polymyositis and dermatomyositis; polychondritis;

Primary glomerulonephritis;

Multiple sclerosis;

Autoimmune hepatitis, primary biliary cirrhosis/autoimmune cholangiopathy,

Hyper acute rejection of transplanted organs;

Chronic rejection of graft or transplants;

Chronic Graft versus Host reaction/disease after transplantation of bone marrow cells or hematopoietic precursor cells.

Additionally of interest are diseases and disorders for which the mechanism is shared between activation/proliferation of T-cells and activation/proliferation of innate immune cells and other inflammatory cellular subpopulations (including myeloid cells such as macrophages or granulocytes) and resident cells (such as fibroblasts and endothelial cells), including:

COPD, idiopathic pulmonary fibrosis, interstitial lung disease, sarcoidosis;

Adult onset Still's disease, juvenile idiopathic arthritis, Systemic sclerosis, CREST syndrome where B cells and pathogen antibodies may also play a role; the Sweet syndrome; Takayasu arteritis, temporal arteritis/giant cell arteritis;

Ulcerative cholangitis, inflammatory bowel disease (IBD) including Crohn's disease and ulcerative colitis, primary sclerosing cholangitis.

Also of interest are diseases and disorders for which the mechanism remains poorly characterized but involves the activation and proliferation of T-cells, including:

Alzheimer's disease, cardiovascular syndrome, type 2 diabetes, restenosis, chronic fatigue immune dysfunction syndrome (CFIDS).

Autoimmune Lymphoproliferative disorders, including:

Autoimmune Lymphoproliferative Syndrome and X-linked lymphoproliferative disease.

Suitably the disease or disorder is selected from: inflammatory skin diseases such as psoriasis or lichen planus; acute and/or chronic GVHD such as steroid resistant acute GVHD; acute lymphoproliferative syndrome; systemic lupus erythematosus, lupus nephritis or cutaneous lupus; or transplantation. In addition, the disease or disorder may be selected from myasthenia gravis, multiple sclerosis, and scleroderma/systemic sclerosis.

The compounds of formula (I) may be used in the treatment of cancer.

Thus, in one embodiment there is provided a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Suitably the cancer is a haematological cancer, such as Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) or chronic lymphocytic leukemia.

Alternatively, the cancer is a non-haematological cancer, such as selected from the group consisting of bladder cancer, breast, melanoma, neuroblastoma, malignant pleural mesothelioma, and sarcoma.

In addition, compounds of formula (I) may be used in enhancing recovery from vascular injury or surgery and reducing morbidity and mortality associated with neointima and restenosis in a subject. For example, the compounds of formula (I) may be used in preventing, reducing, or inhibiting neointima formation. A medical device may be treated prior to insertion or implantation with an effective amount of a composition comprising a compound of formula (I) in order to prevent, reduce, or inhibit neointima formation following insertion or implantation of the device or graft into the subject. The device can be a device that is inserted into the subject transiently, or a device that is implanted permanently. In some embodiments, the device is a surgical device. Examples of medical devices include, but are not limited to, needles, cannulas, catheters, shunts, balloons, and implants such as stents and valves.

Suitably the subject is a mammal, in particular the subject is a human.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prophylaxis of a disease or disorder as described herein.

In a further embodiment, there is provided a method for the prophylaxis or treatment of a disease or disorder as described herein, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder as described herein.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts and/or solvates and/or derivatives thereof may be administered topically, for example to the eye, gut or skin. Thus, in an embodiment there is provided a pharmaceutical composition comprising a compound of the invention optionally in combination with one or more topically acceptable diluents or carriers.

A pharmaceutical composition of the invention may be delivered topically to the skin. Compositions suitable for transdermal administration include ointments, gels and patches. Such a pharmaceutical composition may also suitably be in the form of a cream, lotion, foam, powder, paste or tincture.

The pharmaceutical composition may suitably include vitamin D3 analogues (e.g. calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid.

A pharmaceutical composition of the invention may be delivered topically to the eye. Such a pharmaceutical composition may suitably be in the form of eye drops or an ointment.

A pharmaceutical composition of the invention may be delivered topically to the gut. Such a pharmaceutical composition may suitably be delivered orally, such as in the form of a tablet or a capsule, or rectally, such as in the form of a suppository.

Suitably, delayed release formulations are in the form of a capsule.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil.

The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Suitably, the composition is in unit dose form such as a tablet, capsule or ampoule.

The composition may for example contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 2000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment or prophylaxis of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered separately, sequentially or simultaneously by any convenient route.

Optimal combinations may depend on the disease or disorder. Possible combinations include those with one or more active agents selected from the list consisting of: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, sirolimus, methotrexate, azathioprine mycophenolate mofetil, leflunomide, cyclophosphamide, 6-mercaptopurine or anti-lymphocyte (or thymocyte) globulins); anti-TNF-alpha antibodies (e.g., infliximab, adalimumab, certolizumab pegol or golimumab); anti-IL12/IL23 antibodies (e.g., ustekinumab); anti-IL6 or anti-IL6R antibodies, anti-IL17 antibodies or small molecule IL12/IL23 inhibitors (e.g., apilimod); Antialpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK inhibitors including JAK1 and JAK3 inhibitors (e.g., tofacitinib, baricitinib, R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071).

For cancer, the further pharmaceutically acceptable active ingredient may be selected from anti-mitotic agents such as vinblastine, paclitaxel and docetaxel; alkylating agents, for example cisplatin, carboplatin, dacarbazine and cyclophosphamide; antimetabolites, for example 5-fluorouracil, cytosine arabinoside and hydroxyurea; intercalating agents for example adriamycin and bleomycin; topoisomerase inhibitors for example etoposide, topotecan and irinotecan; thymidylate synthase inhibitors for example raltitrexed; PI3 kinase inhibitors for example idelalisib; mTor inhibitors for example everolimus and temsirolimus; proteasome inhibitors for example bortezomib; histone deacetylase inhibitors for example panobinostat or vorinostat; and hedgehog pathway blockers such as vismodegib.

The further pharmaceutically acceptable active ingredient may be selected from tyrosine kinase inhibitors such as, for example, axitinib, dasatinib, erlotinib, imatinib, nilotinib, pazopanib and sunitinib.

Anticancer antibodies may be included in a combination therapy and may be selected from the group consisting of olaratumab, daratumumab, necitumumab, dinutuximab, traztuzumab emtansine, pertuzumab, obinutuzumab, brentuximab, ofatumumab, panitumumab, catumaxomab, bevacizumab, cetuximab, tositumomab, traztuzumab, gentuzumab ozogamycin and rituximab.

Compounds or pharmaceutical compositions of the invention may also be used in combination with radiotherapy.

Some of the combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Medical Devices

In an embodiment, compounds of the invention or pharmaceutical compositions comprising said compounds may be formulated to permit incorporation into the medical device, thus providing application of the compound or composition directly to the site to prevent or treat conditions disclosed herein.

In an embodiment, the compounds of the invention or pharmaceutical composition thereof is formulated by including it within a coating onto the medical device. There are various coatings that can be utilized such as, for example, polymer coatings that can release the compound over a prescribed time period. The compound, or a pharmaceutical composition thereof, can be embedded directly within the medical device. In some embodiments, the compound is coated onto or within the device in a delivery vehicle such as a microparticle or liposome that facilitates its release and delivery. In some embodiments, the compound or pharmaceutical composition is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. Excessive growth of the adjacent cells following vascular implantation results in a restriction of the vessel particularly at the ends of the implants which results in reduced effectiveness of the implants. If a vascular implant is inserted into a human artery for the elimination of for example an arteriosclerotic stenosis, intima hyperplasia can occur within a year at the ends of the vascular implant and results in renewed stenosis ("restenosis").

Accordingly, in some embodiments, the stents are coated or loaded with a composition including a compound of the invention or pharmaceutical composition thereof and optionally a targeting signal, a delivery vehicle, or a combination thereof. Many stents are commercially available or otherwise know in the art.

In some embodiments, the stent is a drug-eluting stent. Various drug eluting stents that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are also coated or impregnated with a compound of the invention, or pharmaceutical composition thereof and one or more additional therapeutic agents, including, but not limited to, antiplatelet agents, anticoagulant agents, anti-inflammatory agents, antimicrobial agents, antimetabolic agents, additional antineointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Sousa et al. (2003) and Salu et al. (2004).

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon-γ Ib, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 17-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma. It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labelled compounds, barium sulfate, gadolinium oxide, bismuth derivatives, zirconium dioxide, cadmium, tungsten, gold tantalum, bismuth, platinum, iridium, and rhodium. These additives may be, but are not limited to, micro- or nano-sized particles or nano particles. Radio-opacity may be determined by fluoroscopy or by x-ray analysis.

A compound of the invention and one or more additional agents, or pharmaceutical composition thereof, can be incorporated into the stent, either by loading the compound and one or more additional agents, or pharmaceutical composition thereof into the absorbable material prior to processing, and/or coating the surface of the stent with the agent(s). The rate of release of agent may be controlled by a number of methods including varying the following: the ratio of the absorbable material to the compound and one or more additional agents, or pharmaceutical composition, the molecular weight of the absorbable material, the composition of the compound and one or more additional agents, or pharmaceutical composition, the composition of the absorbable polymer, the coating thickness, the number of coating layers and their relative thicknesses, and/or the compound and one or more additional agents, or pharmaceutical composition concentration. Top coats of polymers and other materials, including absorbable polymers, may also be applied to active agent coatings to control the rate of release. For example, P4HB can be applied as a top coat on a metallic stent coated with P4HB including an active agent to retard the release of the active agent.

The invention is further exemplified by the following non-limiting examples.

EXAMPLES

Abbreviations used herein are defined below. Any abbreviations not defined are intended to convey their generally accepted meaning.

Abbreviations

Ac acetyl ($C(O)CH_3$)
aq aqueous
Ar Aromatic ring
BEH ethylene bridged hybrid
Bz benzyl ($CH_2$-phenyl)
Boc tert-butyloxycarbonyl protecting group
CSH charged surface hybrid
d doublet
DCM dichloromethane
dioxane 1,4-dioxane
DMF N,N-dimethylformamide
DMSO dimethyl sulfoxide
($ES^+$) electrospray ionisation, positive mode
($ES^-$) electrospray ionisation, negative mode
ESI electrospray ionisation
Et ethyl
g grams
Hal halogen
HATU 1-[bis(dimethylamino)methylene]-1H-1,2,3-triazolo[4,5-b]pyridinium 3-oxid hexafluorophosphate
HPLC high performance liquid chromatography
hr(s) hour(s)
$IC_{50}$ 50% inhibitory concentration
iPr iso-propyl
LCMS liquid chromatography-mass spectrometry
LHMDS lithium hexamethyldisilazide
$(M+H)^+$ protonated molecular ion
$(M-H)^-$ unprotonated molecular ion
M molar concentration
mL millilitre
mm millimiter
mmol millimole
Me methyl
MHz megahertz
min(s) minute(s)
MSD mass selective detector
m/z mass-to-charge ratio
$N_2$ nitrogen gas
nm nanometre
NMR nuclear magnetic resonance (spectroscopy)
P4HB poly-4-hydroxybutyrate
PDA photodiode array
Pd 174 allyl(2-di-tert-butylphosphino-2',4',6'-triisopropyl-1,1'-biphenyl)palladium(II) triflate or [tBuXPhosPd(allyl)]OTf
$PdCl_2$(dppf) [1,1'-bis(diphenylphosphino)ferrocene]dichloropalladium(II)
$Pd(PPh_3)_4$ tetrakis(triphenylphosphine)palladium(0)
PMB 4-methoxybenzyl
prep HPLC preparative high performance liquid chromatography
Ph phenyl
pos/neg positive/negative
q quartet
RF/MS RapidFire Mass Spectrometry
RT room temperature
Rt retention time
RP reverse phase
s singlet $S_NAr$ nucleophilic aromatic substitution
sat saturated
SCX solid supported cation exchange (resin)
Selectfluor N-chloromethyl-N'-fluorotriethylenediammonium bis(tetrafluoroborate)
t triplet
tBu tert-butyl
T3P 2,4,6-tripropyl-1,3,5,2,4,6-trioxatriphosphorinane-2,4,6-trioxide
TFA Trifluoroacetic acid
[t-BuXPhos Pd(allyl)]OTf allyl(2-di-tert-butylphosphino-2',4',6'-triisopropyl-1,1'-biphenyl)palladium(II) triflate
THF tetrahydrofuran
TMSOK potassium trimethylsilanolate
UPLC ultra performance liquid chromatography
UV ultraviolet
v/v volume/volume
VWD variable wave detector
wt weight
um micrometre
uL microlitre
° C. degrees Celsius General Procedures All starting materials and solvents were obtained either from commercial sources or prepared according to the literature. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 um) cartridges using the amount indicated. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Prep HPLC

Acidic Prep

Waters X-Select CSH column C18, 5 um (19×50 mm), flow rate 28 mL $min^{-1}$ eluting with a $H_2O$-MeCN gradient containing 0.1% v/v formic acid over 6.5 min using UV detection at 254 nm.

Basic Prep

Waters X-Bridge Prep column C18, 5 um (19×50 mm), flow rate 28 mL $min^{-1}$ eluting with a 10 mM $NH_4HCO_3$-MeCN gradient over 6.5 min using UV detection at 254 nm.

Analytical Methods

Reverse Phase HPLC Conditions for the LCMS Analytical Methods

HPLC acidic: Acidic LCMS 4 minute (5-95%)

Analytical LCMS was carried out using a Waters X-Select CSH C18, 2.5 um, 4.6×30 mm column eluting with a gradient of 0.1% Formic acid in MeCN in 0.1% Formic acid in water. The gradient from 5-95% 0.1% Formic acid in MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

HPLC basic: Basic LCMS 4 minute (5-95%)

Analytical LCMS was carried out using a Waters X-Select BEH C18, 2.5 um, 4.6×30 mm column eluting with a gradient of MeCN in aqueous 10 mM ammonium bicarbonate. The gradient from 5-95% MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

Reverse Phase HPLC Conditions for the UPLC Analytical Methods

UPLC acidic: Acidic UPLC 3 minute

Analytical UPLC/MS was carried out using a Waters Acquity CSH C18, 1.7 um, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Acidic UPLC 2: Acidic UPLC 1 minute

Analytical UPLC/MS was carried out using a Waters Acquity CSH C18, 1.7 um, 2.1×30 mm column eluting with a gradient of 0.1% Formic acid in MeCN in 0.1% Formic acid in water. The gradient is structured with a starting point of 5% MeCN held from 0.0-0.08 minutes. The gradient from 5-95% occurs between 0.08-0.70 minutes with a flush from 0.7-0.8 minutes. A column re-equilibration to 5% MeCN is from 0.8-0.9 minutes. UV spectra of the eluted peaks were measured using an Acquity PDA and mass spectra were recorded using an Acquity QDa detector with ESI pos/neg switching.

UPLC basic: Basic UPLC 3 minute

Analytical UPLC/MS was carried out using a Waters Acquity BEH C18, 1.7 um, 2.1×30 mm column eluting with a gradient of MeCN in aqueous 10 mM Ammonium Bicarbonate. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Basic UPLC 2: Basic UPLC 1 minute

Analytical UPLC/MS was carried out using a WatersAcquity BEH C18, 1.7 um, 2.1×30 mm column eluting with a gradient of MeCN in aqueous 10 mM Ammonium Bicarbonate. The gradient is structured with a starting point of 5% MeCN held from 0.0-0.08 minutes. The gradient from 5-95% occurs between 0.08-0.70 minutes with a flush from 0.7-0.8 minutes. A column re-equilibration to 5% MeCN is from 0.8-0.9 minutes. UV spectra of the eluted peaks were measured using an Acquity PDA and mass spectra were recorded using an Acquity QDa detector with ESI pos/neg switching.

Column temperature is 40° C. in all runs. Injection volume is 3 uL and the flow rate is 0.77 mL/min. PDA scan from 210-400 nm on all runs.

Normal Phase HPLC Conditions for the Chiral Analytical Methods

Chiral IC3 method: Chiral HPLC (Diacel Chiralpak IC, 5 um, 4.6×250 mm, 1.0 mL/min, 25-70% EtOH (0.2% TFA) in iso-hexane (0.2% TFA) Chiral IC5 method: Chiral HPLC (Diacel Chiralpak IC, 5 um, 4.6×250 mm, 1.0 mL/min, 20% EtOH (0.2% TFA) in iso-hexane (0.2% TFA).

Reverse Phase HPLC Conditions for the Chiral Analytical Methods Chiral IC6 method: Chiral HPLC (Diacel Chiralpak IC, 5 um, 4.6×250 mm, 1.0 mL/min, 50% MeCN (0.1% formic acid) in water (0.1% formic acid).

$^1$H NMR Spectroscopy $^1$H NMR spectra were acquired on a Bruker Avance III spectrometer at 400 MHz or Bruker Avance III HD spectrometer at 500 MHz using residual undeuterated solvent as reference and unless specified otherwise were run in DMSO-d6.

Preparation of Intermediates

Known synthetic intermediates were procured from commercial sources or were obtained using published literature procedures. Additional intermediates were prepared by the representative synthetic processes described herein.

Preparation of Bi-Ester Intermediates

DMSO-d6) δ 8.83 (d, J=5.1 Hz, 1H), 7.65 (d, J=5.1 Hz, 1H), 5.21 (s, 1H), 3.73 (s, 3H), 1.42 (s, 9H).

Decarboxylation of Chloro-Pyrimidines

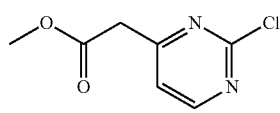

Methyl 2-(2-chloropyrimidin-4-yl)acetate INTC4

TFA (55.3 mL, 717 mmol) was added dropwise to an ice-cooled, stirred solution of 1-tert-butyl 3-methyl 2-(2-chloropyrimidin-4-yl)malonate INTC1 (12.1 g, 42.2 mmol) in DCM (50 mL). The reaction was stirred at 25° C. for 1 hr and then concentrated in vacuo. The residue was dissolved in EtOAc (200 mL), and basified with NaHCO$_3$ (200 mL), the organic layer was isolated and passed through a phase separator, the solvent was removed in vacuo. The crude product was purified by chromatography on silica gel (220 g cartridge, 0-50% EtOAc/iso-hexane) to afford methyl 2-(2-chloropyrimidin-4-yl)acetate (7.12 g, 37.8 mmol, 90% yield) as a pale yellow oil. Rt 1.16 mins (HPLC acidic); m/z 187 (M+H)$^+$ (ES$^+$); 1H NMR (500 MHz, DMSO-d6) δ 8.76 (d, J=5.0 Hz, 1H), 7.60 (d, J=5.0 Hz, 1H), 3.96 (s, 2H), 3.66 (s, 3H).

Method A: Decarboxylation of Chloro-Heterocycles Such as Chloro-Pyrimidines

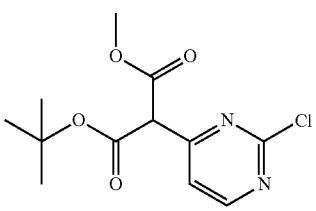

1-(tert-Butyl) 3-methyl 2-(2-chloropyrimidin-4-yl)malonate INTC1

NaH (60 wt % in mineral oil, 5.10 g, 128 mmol) was added portionwise to an ice-cooled, stirred solution of tert-butyl methyl malonate (20.5 mL, 121 mmol) in THF (160 mL). The reaction was stirred at 0° C. for 20 mins then at RT for 60 mins until evolution of hydrogen ceased. 2,4-Dichloropyrimidine (10 g, 67.1 mmol) was then added and the resulting mixture was stirred at 70° C. for 3 hrs. The reaction was allowed to cool, partitioned between NH$_4$Cl (sat. aq, 500 mL) and EtOAc (500 mL), the two phases were separated and the organic layer was passed through a phase separator. The crude product was purified by chromatography on silica gel (220 g column, 0-30% EtOAc/iso-hexane) to afford 1-tert-butyl 3-methyl 2-(2-chloropyrimidin-4-yl) malonate (13.1 g, 44.3 mmol, 66% yield) as a clear pale yellow oil; Rt 2.09 mins (HPLC acidic); m/z 230 (M+H-tBu)$^+$ (ES$^+$) and 287 (M+H)$^+$ (ES$^+$); $^1$H NMR (400 MHz,

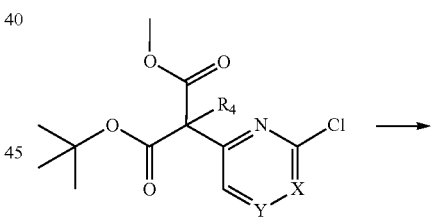

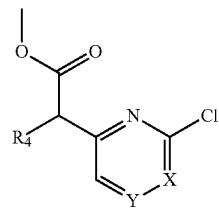

TFA (10 eq) was added dropwise to an ice-cooled, stirred solution of malonate derivative (1 eq) in DCM (15 volumes). The reaction vessel was stirred at RT for 18 hrs and then concentrated. The crude product was purified by normal phase chromatography.

TABLE 1

The following intermediates were made according to Method A.

| INTC | Name/Structure (All examples containing chiral centres are racemates unless stated) | Synthesis Method, [LCMS Method], m/z (M + H)⁺, (Rt/min) | ¹H NMR Chemical Shift Data (DMSO-d6 unless stated) |
|---|---|---|---|
| INTC60 | methyl 2-(2-chloropyrimidin-4-yl)-4-methoxybutanoate | Method A using INTC16, [UPLC acidic], M + Na $^{35}$Cl isotope 267 (0.94). | 8.76 (d, J = 5.0 Hz, 1H), 7.60 (d, J = 5.0 Hz, 1H), 3.98-3.94 (m, 1H), 3.63 (s, 3H), 3.37-3.20 (m, 2H), 3.16 (s, 3H), 2.31-2.21 (m, 1H), 2.14-2.03 (m, 1H). |
| INTC61 | methyl 2-(2-chloropyrimidin-4-yl)butanoate | Method A using INTC15, [HPLC acidic], M + H $^{35}$Cl isotope 215 (1.68). | 8.76 (d, J = 5.1 Hz, 1H), 7.60 (d, J = 5.1 Hz, 1H), 3.87 (t, J = 7.5 Hz, 1H), 3.63 (s, 3H), 2.08-1.98 (m, 1H), 1.93-1.83 (m, 1H), 0.83 (t, J = 7.4 Hz, 3H). |

Method B: Alkylation

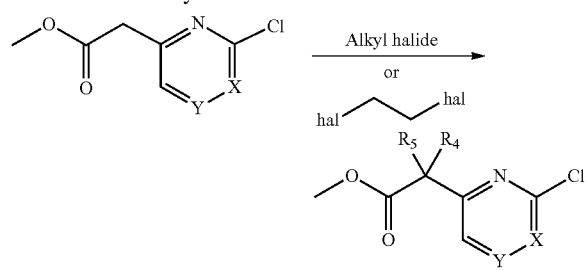

Base (2.5-5 eq) was added to an ice-cooled, stirred mixture of methyl 2-(2-chloropyrimidin-4-yl)acetate (1 eq) in appropriate polar aprotic solvent such as DMF or acetone (10 volumes). After 20 min, alkyl halide (1-5 eq) or hal-CH$_2$—CH$_2$-hal (1-1.5 eq) was added. The reaction vessel was stirred at 0° C. for 30 mins then at RT for 2 hrs. The reaction was quenched with NH$_4$Cl (aq) or 1 M HCl (aq), stirred for 20 mins then extracted with EtOAc. The organic phases were dried (phase separator) and concentrated. The crude product was purified by normal phase chromatography.

TABLE 2

The following intermediates were made according to Method B.

| INTC | Name/Structure (All examples containing chiral centres are racemates unless stated) | Synthesis Method, [LCMS Method], m/z (M + H)⁺, (Rt/min) | ¹H NMR Chemical Shift Data (DMSO-d6 unless stated) | Base, RX, solvent |
|---|---|---|---|---|
| INTC14 | methyl-1-(2-chloropyrimidin-4-yl)-cyclopentane-1-carboxylate | Method B using INTC4, [UPLC acidic], 241 (1.32). | 8.79-8.66 (m, 1H), 7.65-7.55 (m, 1H), 3.62 (s, 3H), 2.41-2.25 (m, 2H), 2.21-2.06 (m, 2H), 1.81-1.57 (m, 4H). | NaOH, Br-(n-Bu)-Br DMF |

TABLE 2-continued

The following intermediates were made according to Method B.

| INTC | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) | Base, RX, solvent |
|---|---|---|---|---|
| INTC15 | 1-(tert-butyl) 3-methyl 2-(2-chloropyrimidin-4-yl)-2-ethyl-malonate | Method B using INTC1, [UPLC acidic], 315 (1.58). | 8.83 (d, J = 5.3 Hz, 1H), 7.80 (d, J = 5.3 Hz, 1H), 3.73 (s, 3H), 2.29-2.14 (m, 2H), 1.40 (s, 9H), 0.82 (t, J = 7.4 Hz, 3H). | NaOH, EtBr, DMF |
| INTC16 | 1-(tert-butyl) 3-methyl 2-(2-chloro-pyrimidin-4-yl)-2-(2-methoxyethyl)-malonate | Method B using INTC1, [UPLC acidic], 345 (1.48). | 8.83 (dd, J = 5.2, 1.0 Hz, 1H), 7.83 (d, J = 5.3 Hz, 1H), 3.72 (s, 3H), 3.31-3.24 (m, 2H), 3.11 (s, 3H), 2.47-2.40 (m, 2H), 1.39 (s, 9H). | NaOH, BrCH$_2$CH$_2$OMe, DMF |
| INTC117 | Methyl 2-(6-chloropyrazin-2-yl)-butanoate | Method B using commercial methyl 2-(6-chloropyrazin-2-yl)acetate [HPLC acidic], 215 35Cl isotope (1.84). | 8.73 (s, 1H), 8.70 (s, 1H), 3.95 (dd, J = 8.1, 7.0 Hz, 1H), 3.62 (s, 3H), 2.13-2.01 (m, 1H), 1.96-1.84 (m, 1H), 0.83 (t, J = 7.4 Hz, 3H). | K$_2$CO$_3$, EtBr, acetone |

Heterocycle Formation Via Alkylation

Methyl 4-(2-chloropyrimidin-4-yl)tetrahydro-2H-pyran-4-carboxylate INTC52

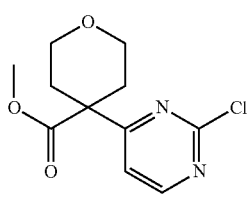 [SMILES: COC(=O)C1(c2ccnc(Cl)n2)CCOCC1]

To a solution of methyl 2-(2-chloropyrimidin-4-yl)acetate INTC4 (2.0 g, 10.7 mmol) in DMF (10 mL, 10.7 mmol) at 0° C. was added NaOH (0.986 g, 24.6 mmol). The reaction mixture was stirred at 0° C. for 20 mins then 1-bromo-2-(2-bromoethoxy)ethane (1.8 mL, 12.9 mmol) was added. The reaction was stirred at RT for 23 hrs. The reaction mixture was acidified using 1 M HCl (aq, 53.6 mL, 53.6 mmol) before extracting with DCM (70 mL). The phases were separated using a phase separator cartridge and the aqueous was extracted with further DCM (2×50 mL). The combined organics were concentrated in vacuo. The crude product was purified by chromatography on silica gel (80 g column, 0-50% EtOAc/iso-hexane) to afford methyl 4-(2-chloropyrimidin-4-yl)tetrahydro-2H-pyran-4-carboxylate (1.83 g, 5.57 mmol, 52% yield) as a yellow oil. Rt 1.56 min (HPLC, acidic); m/z 257 ($^{35}$Cl M+H)+ (ES+); 1H NMR (500 MHz, DMSO-d6) δ 8.80 (d, J=5.3 Hz, 1H), 7.69 (d, J=5.3 Hz, 1H), 3.72-3.67 (m, 2H), 3.66 (s, 3H), 3.55-3.50 (m, 2H), 2.33-2.22 (m, 2H), 2.16-2.06 (m, 2H).

Heterocycle Formation Via Enolate S$_N$AR 1-tert-Butyl 4-methyl 4-(2-chloropyrimidin-4-yl)piperidine-1,4-dicarboxylate INTC66

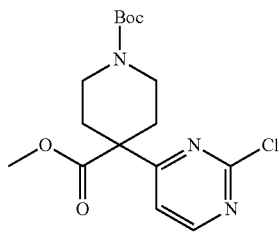 [SMILES: COC(=O)C1(c2ccnc(Cl)n2)CCN(C(=O)OC(C)(C)C)CC1]

LiHMDS (1.61 mL, 1.61 mmol) was added in one portion to an ice-cooled, stirred solution of 1-tert-butyl 4-methyl piperidine-1,4-dicarboxylate (340 mg, 1.40 mmol) and 2,4-dichloropyrimidine (200 mg, 1.34 mmol) in THF (10 mL). The reaction mixture was allowed to warm up to RT and stirred for 2 hrs. The reaction was quenched by addition of NaH$_2$PO$_4$ (aq, 1M, 3 mL). The product was extracted with DCM (2×10 mL). The combined organic extracts were dried via a hydrophobic phase separator and concentrated in vacuo. The crude product was purified by chromatography on silica gel (24 g column, 0-50% EtOAc/iso-hexane) to afford 1-tert-butyl 4-methyl 4-(2-chloropyrimidin-4-yl)piperidine-1,4-dicarboxylate (315 mg, 0.66 mmol, 49% yield) as a colourless oil. Rt 2.29 min (HPLC, acidic); m/z 255 ($^{35}$Cl M-Boc+H)$^+$ (ES$^+$); $^1$H NMR (500 MHz, DMSO-d6) δ 8.79 (d, J=5.3 Hz, 1H), 7.68 (d, J=5.3 Hz, 1H), 3.69-3.59 (m, 5H), 3.13 (s, 2H), 2.26-2.22 (m, 2H), 2.06-2.00 (m, 2H), 1.40 (s, 9H).

Hydrolysis of Chloro-Pyrimidines

Lithium 2-(2-chloropyrimidin-4-yl)-4-methoxybutanoate
INTC68

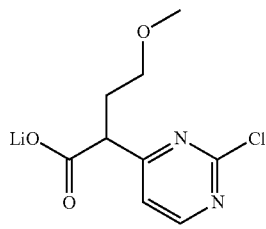

To a solution of methyl 2-(2-chloropyrimidin-4-yl)-4-methoxybutanoate INTC60 (479 mg, 1.96 mmol) in THF (5 mL) and MeOH (2.5 mL) was added a solution of LiOH (56 mg, 2.35 mmol) in water (3 mL). The reaction mixture was stirred at RT for 72 hrs. The reaction mixture was concentrated in vacuo to give lithium 2-(2-chloropyrimidin-4-yl)-4-methoxybutanoate (441 mg, 1.49 mmol, 76% yield) as a colourless solid. Rt 1.34 min (HPLC acidic); m/z 231 (as free acid $^{35}$Cl M+H)$^+$ (ES$^+$); $^1$H NMR (500 MHz, DMSO-d6) δ 8.64 (d, J=5.1 Hz, 1H), 7.48 (d, J=5.1 Hz, 1H), 3.39-3.33 (m, 1H), 3.22 (s, 3H), 2.82-2.75 (m, 2H), 1.96-1.85 (m, 2H).

Method C: Formation of Sulfonamides from Aromatic Halides

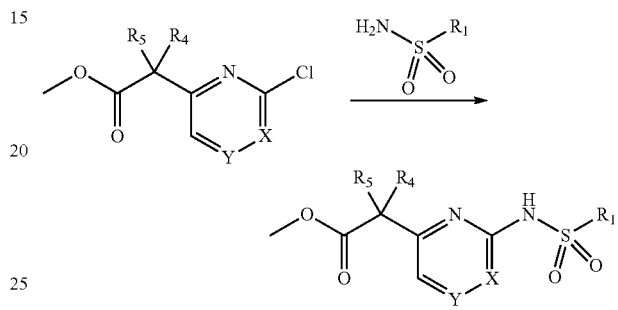

2-Chloropyrimidine intermediate (1 eq), sulfonamide (1.2 eq) and base (2 eq) were dissolved in dioxane (40 volumes). The mixture was degassed (N$_2$, 5 mins) then catalyst (5 mol %) was added. The resulting mixture was heated under nitrogen at 90° C. for 2 hrs. The mixture was filtered, washing with EtOAc or DCM and the resulting filtrate was concentrated. The crude product was purified by normal phase chromatography or trituration using a suitable solvent.

TABLE 3

| | | | | |
|---|---|---|---|---|
| | The following intermediates were made according to Method C. | | | |
| INTC | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) | Catalyst Base Solvent |
| INTC29 | methyl 1-2-(cyclopropanesulfonamido)pyrimidin-4-yl)cyclopentane-1-carboxylate | Method C using INTC14, [UPLC acidic], 326 (1.17). | 11.23 (s, 1H), 8.59-8.45 (m, 1H), 7.17-7.05 (m, 1H), 3.61 (s, 3H), 3.25-3.12 (m, 1H), 2.40-2.24 (m, 2H), 2.21-2.08 (m, 2H), 1.73-1.59 (m, 4H), 1.18-0.96 (m, 4H). | Pd 174, Cs$_2$CO$_3$, dioxane |
| INTC30 | 1-(tert-butyl) 3-methyl 2-(2-(cyclopropanesulfonamido)pyrimidin-4-yl)-2-ethylmalonate | Method C using INTC15, [UPLC acidic], 400 (1.40). | 11.30 (s, 1H), 8.62 (d, J = 5.3 Hz, 1H), 7.35 (d, J = 5.3 Hz, 1H), 3.71 (s, 3H), 3.21-3.10 (m, 1H), 2.30-2.10 (m, 2H), 1.41 (s, 9H), 1.18-0.97 (m, 4H), 0.83 (t, J = 7.4 Hz, 3H). | Pd 174, Cs$_2$CO$_3$, dioxane |

TABLE 3-continued

*The following intermediates were made according to Method C.*

| INTC | Name/Structure (All examples containing chiral centres are racemates unless stated) | Synthesis Method, [LCMS Method], m/z (M + H)⁺, (Rt/min) | $^1$H NMR Chemical Shift Data (DMSO-d6 unless stated) | Catalyst Base Solvent |
|---|---|---|---|---|
| INTC53 | methyl 4-(2-(cyclopropanesulfonamido)-pyrimidin-4-yl)tetrahydro-2H-pyran-4-carboxylate | Method C using INTC52 [UPLC, acidic], 342 (0.88). | 11.30 (s, 1H), 8.61 (d, J = 5.3 Hz, 1H), 7.20 (d, J = 5.3 Hz, 1H), 3.79-3.71 (m, 2H), 3.67 (s, 3H), 3.52-3.48 (m, 2H), 3.25-3.15 (m, 1H), 2.24-2.21 (m, 2H), 2.13-2.03 (m, 2H), 1.08-1.01 (m, 2H), 0.91-0.87 (m, 2H). | Pd 174, Cs$_2$CO$_3$, dioxane |
| INTC74 | methyl 2-fluoro-2-(2-(methylsulfonamido)-pyrimidin-4-yl)butanoate | Method C using INTC85, [HPLC acidic], 292 (1.52). | 11.56 (s, 1H), 8.74 (d, J = 5.1 Hz, 1H), 7.31 (d, J = 5.1 Hz, 1H), 3.74 (s, 3H), 3.37 (s, 3H), 2.43-2.17 (m, 2H), 0.88 (t, J = 7.3 Hz, 3H). | Pd-174 Cs$_2$CO$_3$, dioxane |
| INTC77 | 1-tert-butyl 4-methyl 4-(2-(cyclopropanesulfon-amido)pyrimidin-4-yl)piperidine-1,4-dicarboxylate | Method C using INTC66, [HPLC acidic], 385 (M − tBu + H) (2.08). | 11.30 (s, 1H), 8.59 (d, J = 5.3 Hz, 1H), 7.19 (d, J = 5.3 Hz, 1H), 3.74-3.67 (m, 1H), 3.67 (s, 3H), 3.24-3.15 (m, 1H), 2.53-2.48 (m, 2H), 2.26-2.19 (m, 3H), 2.03-1.92 (m, 2H), 1.40 (s, 9H), 1.15-1.08 (m, 2H), 1.08-1.00 (m, 2H). | Pd-174 Cs$_2$CO$_3$, dioxane |
| INTC127 | Methyl 4-(6-(cyclopropanesulfonamido)pyrazin-2-yl)tetrahydro-2H-pyran-4-carboxylate | Method C using INTC123, [HPLC acidic], 342 (1.45). | 11.11 (s, 1H), 8.34-7.68 (m, 2H), 3.78-3.67 (m, 2H), 3.63 (s, 3H), 3.52-3.44 (m, 2H), 3.02-2.98 (m, 1H), 2.25 (s, 2H), 2.09 (s, 2H), 1.09-0.85 (m, 4H). | Pd-174, Cs2CO3, dioxane |
| INTC130 | Methyl 2-(6-(cyclopropanesulfonamido)pyrazin-2-yl)-2-fluorobutanoate | Method C using INTC124, [UPLC acidic], 318 (1.08). | 11.29 (s, 1H), 8.48 (s, 1H), 8.33 (s, 1H), 3.73 (s, 3H), 3.10-3.04 (m, 1H), 2.45-2.27 (m, 2H), 1.24-1.00 (m, 4H), 0.91 (t, J = 7.4 Hz, 3H). | Pd-174, Cs2CO3, dioxane |

Method D: Decarboxylation of Pyrimidines Bearing Sulfonamides

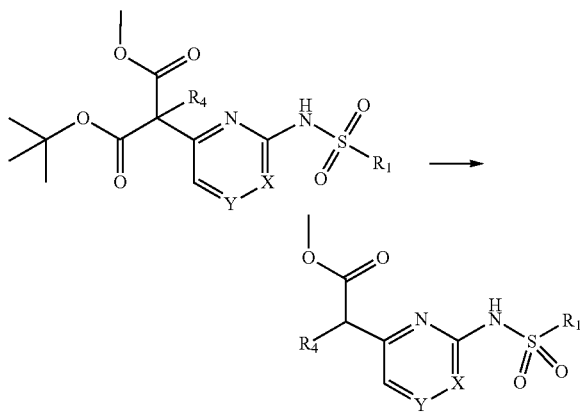

TFA (10 eq) was added dropwise to an ice-cooled, stirred solution of malonate derivative (1 eq) in DCM (15 volumes). The reaction vessel was stirred at RT for 18 hrs and then concentrated. The crude product was purified by normal phase chromatography.

1-(Bromomethyl)-4-methoxybenzene (0.470 mL, 3.34 mmol) was added into a stirring heterogeneous mixture of methyl 2-(2-(cyclopropanesulfonamido)pyrimidin-4-yl)butanoate (1 g, 3.34 mmol) INTC35 and $K_2CO_3$ (0.46 g, 3.34 mmol) in DMF (20 mL). The resulting reaction mixture was stirred at RT for 18 hrs and was then poured into water (200 mL) and extracted with EtOAc (3×50 mL). The organic extract was washed with water (100 mL) and brine (100 mL), dried over $MgSO_4$, filtered and solvent removed in vacuo. The crude product was purified by chromatography on silica gel (40 g column, 0-50% EtOAc/iso-hexane) to afford methyl 2-(2-(N-(4-methoxybenzyl) cyclopropanesulfonamido)pyrimidin-4-yl)butanoate (844 mg, 1.95 mmol, 58% yield) as a colourless oil. Rt 2.43 min (HPLC, acidic); m/z 420 (M+H)$^+$ (ES$^+$); $^1$H NMR (500 MHz, DMSO-d6) δ 8.64 (d, J=5.1 Hz, 1H), 7.25 (d, J=8.3 Hz, 2H), 7.19 (d, J=5.1 Hz, 1H), 6.86 (d, J=8.3 Hz, 2H), 5.17-5.02 (m, 2H), 3.71 (s, 3H), 3.64-3.55 (m, 4H), 2.05-1.93 (m, 2H), 1.89-1.76 (m, 1H), 1.10-0.96 (m, 4H), 0.82 (t, J=7.3 Hz, 3H).

TABLE 4

The following intermediate was made according to Method D.

| INTC | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| INTC35 | methyl 2-(2-(cyclopropanesulfonamido)-pyrimidin-4-yl)butanoate | Method D using INTC30, [UPLC acidic], 300 (0.99). | 11.26 (s, 1H), 8.57 (d, J = 5.1 Hz, 1H), 7.13 (d, J = 5.1 Hz, 1H), 3.74 (t, J = 7.5 Hz, 1H), 3.62 (s, 3H), 3.26-3.15 (m, 1H), 2.06-1.93 (m, 1H), 1.92-1.77 (m, 1H), 1.19-0.96 (m, 4H), 0.85 (t, J = 7.4 Hz, 3H). |

PMB Protection

Methyl 2-(2-(N-(4-methoxybenzyl)cyclopropanesulfonamido)pyrimidin-4-yl)butanoate INTC48

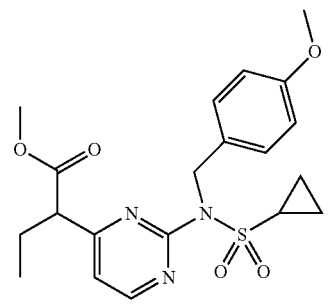 [SMILES: CCC(C(=O)OC)c1ccnc(N(Cc2ccc(OC)cc2)S(=O)(=O)C2CC2)n1]

Fluorination

Methyl 2-fluoro-2-(2-(N-(4-methoxybenzyl)cyclopropanesulfonamido)pyrimidin-4-yl)butanoate INTC49

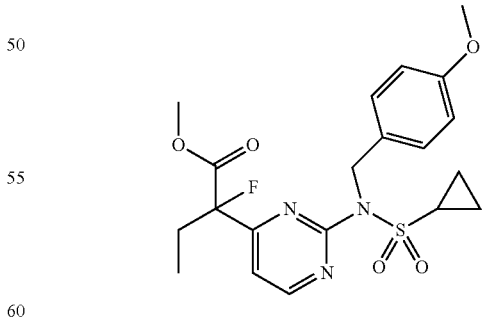

To a solution of methyl 2-(2-(N-(4-methoxybenzyl)cyclopropanesulfonamido)pyrimidin-4-yl)butanoate INTC48 (400 mg, 0.95 mmol) in THF (10 mL) at −78° C. was added LHMDS (1.19 mL, 1.19 mmol, 1 M in THF) dropwise over 5 min. The resulting mixture was warmed to RT and stirred for 1 hr. The solution was cooled down to −78° C. again and a solution of N-fluoro-N-(phenylsulfonyl)benzenesulfonamide (376 mg, 1.19 mmol) in THF (3 mL) was added dropwise over 5 min. The resulting mixture was warmed to RT and stirred for 1 hr. The solution was diluted with sat. NaHCO₃ (aq, 100 mL) and EtOAc (100 mL) and the phases were separated. The aqueous phase was extracted with EtOAc (2×50 mL). The combined organic layers were dried over Na₂SO₄, filtered and the solvent was removed in vacuo. The crude product was purified by chromatography on silica gel (24 g column, 0-50% EtOAc/iso-hexane) to afford methyl 2-fluoro-2-(2-(N-(4-methoxybenzyl)cyclopropanesulfonamido)pyrimidin-4-yl)butanoate (390 mg, 0.865 mmol, 91% yield) as a clear oil. Rt 2.48 min (HPLC, acidic); m/z 438 (M+H)⁺ (ES⁺); ¹H NMR (500 MHz, DMSO-d6) δ 8.81 (d, J=5.1 Hz, 1H), 7.37 (dd, J=5.1, 1.5 Hz, 1H), 7.29-7.19 (m, 2H), 6.90-6.83 (m, 2H), 5.17-5.03 (m, 2H), 3.72 (s, 3H), 3.69 (s, 3H) 3.65-3.57 (m, 1H), 2.40-2.14 (m, 2H), 1.11-0.97 (m, 4H), 0.84 (t, J=7.4 Hz, 3H).

INTC49 which is enantio-enriched can be made using the following method:

To a solution of methyl 2-(2-(N-(4-methoxybenzyl)cyclopropanesulfonamido)pyrimidin-4-yl)butanoate INTC48 (0.066 g, 0.157 mmol) in THF (2.5 mL) at −40° C. was added LHMDS (0.189 mL, 0.189 mmol) dropwise over 5 mins. The resulting mixture was warmed to RT and stirred for 1 hr. A second solution was prepared of (−)-Cinchonidine (0.069 g, 0.236 mmol) and Selectfluor (0.072 g, 0.205 mmol) in MeCN (2.5 mL), which was stirred at RT for 30 mins. The solution of fluorinating agent was then cooled to −40° C. and the solution of deprotonated ester was added dropwise over 5 mins. The reaction mixture was stirred at −40° C. for 1 h and warmed to RT as the cooling bath expired over 2 h. The reaction mixture was stirred at RT for 20 h. The reaction mixture was diluted with sat. NaHCO₃ (aq, 10 mL) and EtOAc (20 mL). The phases were separated and the organics were washed with further sat. NaHCO₃ (aq, 10 mL) then 1 M HCl (aq, 10 mL). The combined organics were dried (MgSO₄), filtered and concentrated in vacuo. The crude product was purified by chromatography on silica gel (4 g cartridge, 0-50% EtOAc/iso-hexane) to afford methyl 2-fluoro-2-(2-(N-(4-methoxybenzyl)cyclopropanesulfonamido)pyrimidin-4-yl)butanoate (0.024 g, 0.052 mmol, 33% yield) as a colourless oil. Rt 0.70 min (UPLC 2, acidic); m/z 438 (M+H)⁺ (ES⁺); ¹H NMR (500 MHz, DMSO-d6) δ 8.81 (d, J=5.1 Hz, 1H), 7.37 (dd, J=5.1, 1.5 Hz, 1H), 7.29-7.19 (m, 2H), 6.90-6.83 (m, 2H), 5.17-5.03 (m, 2H), 3.72 (s, 3H), 3.69 (s, 3H) 3.65-3.57 (m, 1H), 2.40-2.14 (m, 2H), 1.11-0.97 (m, 4H), 0.84 (t, J=7.4 Hz, 3H).

Lithium Salt Formation

Lithium 2-fluoro-2-(2-(N-(4-methoxybenzyl)cyclopropanesulfonamido)pyrimidin-4-yl)butanoate INTC50

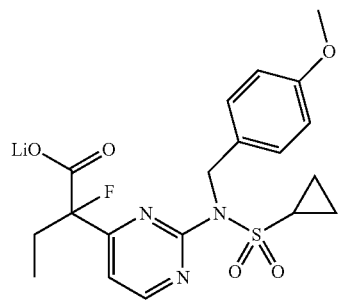

To a solution of methyl 2-fluoro-2-(2-(N-(4-methoxybenzyl)cyclopropanesulfonamido) pyrimidin-4-yl)butanoate INTC49 (1.45 g, 3.31 mmol) in THF (15 mL) and MeOH (7.5 mL) was added a solution LiOH (0.091 g, 3.81 mmol) in water (5 mL). The reaction mixture was stirred at RT for 3 hrs. The reaction mixture was concentrated in vacuo and the resulting yellow oil was taken up into in MeCN (10 mL) and concentrated in vacuo to give lithium 2-fluoro-2-(2-(N-(4-methoxybenzyl)cyclopropanesulfonamido)pyrimidin-4-yl)butanoate (1.46 g, 3.30 mmol, quant. yield) as a pale yellow foam which was used without further purification. Rt 0.95 min (UPLC, basic); m/z 424 (ionizes as COOH, M+H)⁺ (ES⁺); ¹H NMR (500 MHz, DMSO-d6) δ 8.57-8.52 (m, 1H), 7.34-7.28 (m, 2H), 7.20-7.14 (m, 1H), 6.90-6.83 (m, 2H), 5.19-5.04 (m, 2H), 4.14-4.10 (m, 1H), 3.71 (s, 3H), 2.33-2.20 (m, 1H), 2.17-2.08 (m, 1H), 1.15-1.04 (m, 1H), 1.06-0.97 (m, 1H), 0.93-0.80 (m, 2H), 0.80-0.73 (m, 3H).

Tetrahydropyran-Derivative Via Thioether

Methyl 4-(2-(methylthio)pyrimidin-4-yl)tetrahydro-2H-pyran-4-carboxylate INTC178

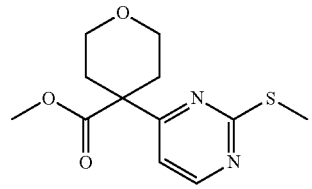

To a solution of 4-chloro-2-(methylthio)pyrimidine (0.55 g, 3.42 mmol) and methyl tetrahydro-2H-pyran-4-carboxylate (494 mg, 3.42 mmol) in THF (5 mL) at 30° C. was added LHMDS (1 M in THF) (4.11 mL, 4.11 mmol) dropwise. The reaction mixture was stirred at 30° C. for 5 min then was poured into water (100 mL) and extracted with EtOAc (2×200 mL). The organic extract was washed with brine (1×100 mL), dried (MgSO₄), filtered and solvent removed in vacuo to afford methyl 4-(2-(methylthio)pyrimidin-4-yl)tetrahydro-2H-pyran-4-carboxylate (915 mg, 3.24 mmol, 95% yield) as a pale yellow oil. Rt 1.74 min (HPLC acidic); m/z 269 (M+H)⁺ (ES⁺); ¹H NMR (500 MHz, DMSO-d6) δ 8.62 (d, J=5.3 Hz, 1H), 7.27 (d, J=5.3 Hz, 1H), 3.76-3.70 (m, 2H), 3.67 (s, 3H), 3.54-3.46 (m, 2H), 2.49 (s, 3H), 2.27-2.20 (m, 2H), 2.14-2.04 (m, 2H).

Methyl 4-(2-(methylsulfonyl)pyrimidin-4-yl)tetrahydro-2H-pyran-4-carboxylate INTC179

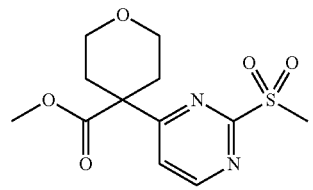

mCPBA (1.60 g, 7.13 mmol) was added portionwise into a stirring solution of methyl 4-(2-(methylthio)pyrimidin-4-yl)tetrahydro-2H-pyran-4-carboxylate INTC178 (915 mg, 3.24 mmol) in DCM (50 mL) and the resulting reaction mixture was stirred at RT for 3 hrs. The reaction mixture was poured into sat. NaHCO₃ (aq, 200 mL) and extracted with DCM (3×100 mL). The organic extract was sequentially washed with sat. NaHCO₃ (aq, 100 mL) and brine (100 mL), dried (MgSO₄), filtered and solvent removed in vacuo to afford methyl 4-(2-(methylsulfonyl)pyrimidin-4-yl)tetrahydro-2H-pyran-4-carboxylate (1.10 g, 3.30 mmol, quant. yield) as thick gum. Rt 1.20 min (HPLC acidic); m/z 301 (M+H)⁺ (ES⁺); ¹H NMR (500 MHz, DMSO-d6) δ 9.09 (d, J=5.3 Hz, 1H), 7.95 (d, J=5.3 Hz, 1H), 3.77-3.70 (m, 2H), 3.68 (s, 3H), 3.60-3.49 (m, 2H), 3.42 (s, 3H), 2.34-2.24 (m, 2H), 2.23-2.13 (m, 2H).

Methyl 4-(2-(cyclopropanesulfonamido)pyrimidin-4-yl)tetrahydro-2H-pyran-4-carboxylate INTC53

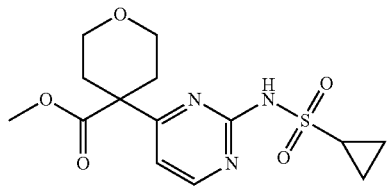 [SMILES: COC(=O)C1(c2ccnc(NS(=O)(=O)C3CC3)n2)CCOCC1]

To a solution of methyl 4-(2-(methylsulfonyl)pyrimidin-4-yl)tetrahydro-2H-pyran-4-carboxylate INTC179 (1.0 g, 3.33 mmol) and cyclopropanesulfonamide (0.52 g, 4.33 mmol) in NMP (100 mL) was added cesium carbonate (3.25 g, 9.99 mmol) and heated to 90° C. for 1 hr. The reaction mixture was cooled to RT and diluted with water (100 mL) and the mixture was washed with MTBE (2×100 mL) and the aqueous was slowly acidified to pH 3 using dilute HCl (20 mL). The resulting precipitate was filtered to afford methyl 4-(2-(cyclopropanesulfonamido)pyrimidin-4-yl)tetrahydro-2H-pyran-4-carboxylate (755 mg, 2.21 mmol, 66% yield) as a colourless solid. Rt. 0.88 (UPLC, acidic), m/z 342 (M+H)⁺ (ES⁺); ¹H NMR (500 MHz, DMSO-d6) δ 11.30 (s, 1H), 8.60 (d, J=5.3 Hz, 1H), 7.20 (d, J=5.3 Hz, 1H), 3.79-3.72 (m, 2H), 3.67 (s, 3H), 3.52-3.44 (m, 2H), 3.25-3.14 (m, 1H), 2.30-2.17 (m, 2H), 2.12-2.04 (m, 2H), 1.14-1.01 (m, 4H).

Amide Formation of Selected Building Blocks

Heterocycle Formation Via Alkylation

Ethyl 4-(6-bromopyridin-2-yl)tetrahydro-2H-pyran-4-carboxylate INTC105

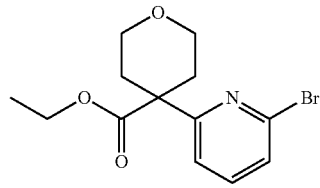 [SMILES: CCOC(=O)C1(c2cccc(Br)n2)CCOCC1]

Prepared as for INTC52 using commercial ethyl 2-(6-bromopyridin-2-yl)acetate (2.51 g, 10.28 mmol) and 1-bromo-2-(2-bromoethoxy)ethane to afford ethyl 4-(6-bromopyridin-2-yl)tetrahydro-2H-pyran-4-carboxylate (52% yield) as a clear oil. Rt 1.42 mins (UPLC basic); m/z 314 (⁷⁹Br M+H)⁺ (ES⁺); ¹H NMR (400 MHz, DMSO-d6) δ 7.80-7.76 (m, 1H), 7.57 (d, J=7.9 Hz, 1H), 7.49 (d, J=7.7 Hz, 1H), 4.12 (q, J=7.1 Hz, 2H), 3.77-3.70 (m, 2H), 3.52-3.45 (m, 2H), 2.30-2.23 (m, 2H), 2.07-2.01 (m, 2H), 1.12 (t, J=7.1 Hz, 3H).

Method I: Buchwald Coupling—Sulfonylation

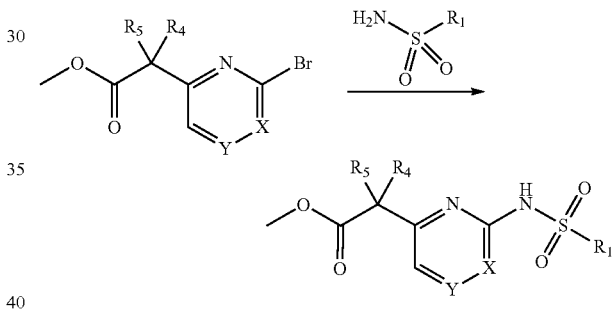

2-Bromopyridine intermediate (1 eq), sulfonamide (1.2 eq) and base (2 eq) were dissolved in dioxane (40 volumes). The mixture was degassed (N₂, 5 mins) then catalyst (5 mol %) was added. The resulting mixture was heated under

TABLE 5

The following intermediate was made according to Method 4 which is described below for the synthesis of compound of formula (I).

| INTC | Name/Structure (All examples containing chiral centres are racemates unless stated) | Synthesis Method, [LCMS Method], m/z (M + H)⁺, (Rt/min) | ¹H NMR Chemical Shift Data (DMSO-d6 unless stated) |
|---|---|---|---|
| INTC89 | 2-(2-chloropyrimidin-4-yl)-N-(5-(6-ethoxypyrazin-2-yl)pyridin-2-yl)-4-methoxybutanamide 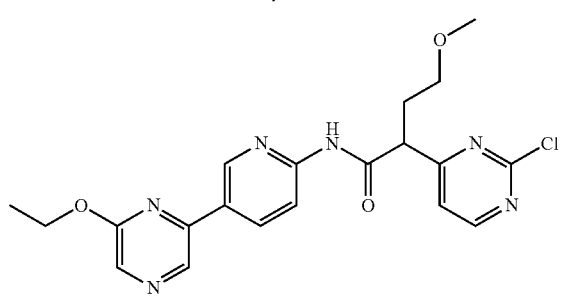 | Method 4 using INTC68 and INTD33 [UPLC acidic], 429 ³⁵Cl isotope (1.38). | 11.12 (s, 1H), 9.10-9.05 (m, 1H), 8.84 (s, 1H), 8.75 (d, J = 5.2 Hz, 1H), 8.53-8.47 (m, 1H), 8.25 (s, 1H), 8.20 (d, J = 8.7 Hz, 1H), 7.68 (d, J = 5.2 Hz, 1H), 4.52-4.44 (m, 2H), 4.34-4.27 (m, 1H), 3.42-3.32 (m, 2H), 3.20 (s, 3H), 2.37-2.26 (m, 1H), 2.20-2.09 (m, 1H), 1.43-1.37 (m, 3H). | nitrogen at 90° C. for 2 hrs. The mixture was filtered, washing with EtOAc or DCM and the resulting filtrate was concentrated. The crude product was purified by normal phase chromatography.

reaction mixture was concentrated in vacuo and the resulting residue was acidified using 1 M HCl (200 mL). The product was extracted using EtOAc (5×100 mL), the combined organics were dried (Na2SO4), filtered and concentrated in

TABLE 6

The following intermediate was made according to Method I.

| INTC | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) | Catalyst, Base, Solvent |
|---|---|---|---|---|
| INTC108 | ethyl 4-(6-(cyclopropanesulfonamido)pyridin-2-yl)-tetrahydro-2H-pyran-4-carboxylate | Method I using INTC105, [HPLC acidic], 355 (1.78). | 10.55 (s, 1H), 7.74-7.70 (m, 1H), 7.05 (d, J = 7.7 Hz, 1H), 6.82 (d, J = 8.1 Hz, 1H), 4.10 (q, J = 7.1 Hz, 2H), 3.82-3.72 (m, 2H), 3.53-3.43 (m, 2H), 3.24-3.16 (m, 1H), 2.33-2.25 (m, 2H), 2.11-2.00 (m, 2H), 1.15-1.06 (m, 5H), 1.05-0.98 (m, 2H). | Pd 174, Cs2CO3, dioxane |

Ester Formation

Methyl 2-(6-chloropyrazin-2-yl)acetate INTC112

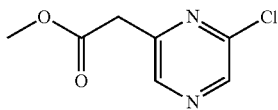

Thionyl chloride (1.15 mL, 15.65 mmol) was added dropwise into a stirring cold solution of 2-(6-chloropyrazin-2-yl)acetic acid (2.70 g, 15.65 mmol) in MeOH (50 mL) at 0° C. After addition the reaction mixture was stirred at RT for 1 hr. The reaction mixture was concentrated in vacuo and the crude residue was diluted with DCM (100 mL) and sequentially washed with sat.

NaHCO3 (aq, 2×100 mL), and brine (100 mL). The organic extract was dried (MgSO4), filtered and solvent removed in vacuo to afford methyl 2-(6-chloropyrazin-2-yl)acetate (2.63 g, 13.67 mmol, 87% yield) as brown oil. Rt 1.25 min (HPLC, acidic); m/z 187 ($^{35}$Cl M+H)+ (ES+); 1H NMR (500 MHz, DMSO-d6) δ 8.74 (s, 1H), 8.68 (s, 1H), 4.00 (s, 2H), 3.66 (s, 3H).

2-(6-(Cyclopropanesulfonamido)pyrazin-2-yl)-2-fluorobutanoic Acid INTC133

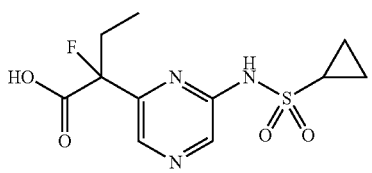 [SMILES: CCC(F)(C(=O)O)c1cncc(NS(=O)(=O)C2CC2)n1]

To a solution of methyl 2-(6-(cyclopropanesulfonamido) pyrazin-2-yl)-2-fluorobutanoate (14.2 g, 44.7 mmol) INTC130 in THF (100 L) was added MeOH (30 mL), and a solution of solution of LiOH (3.21 g, 134 mmol) in water (30 mL). The reaction was stirred at RT for 18 hrs. The vacuo to afford 2-(6-(cyclopropanesulfonamido)pyrazin-2-yl)-2-fluorobutanoic acid (13.87 g, 42.1 mmol, 95% yield) as a thick red paste. Rt 0.89 min (UPLC, acidic); m/z 304 (M+H)+ (ES+); 1H NMR (500 MHz, DMSO-d6) δ 13.74 (s, 1H), 11.23 (s, 1H), 8.45 (s, 1H), 8.33 (s, 1H), 3.15-3.09 (m, 1H), 2.45-2.21 (m, 2H), 1.21-1.15 (m, 1H), 1.15-0.97 (m, 3H), 0.92 (t, J=7.4 Hz, 3H).

Heterocycle Formation Via Alkylation

Methyl 4-(6-chloropyrazin-2-yl)tetrahydro-2H-pyran-4-carboxylate INTC123

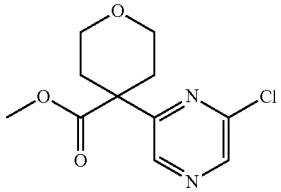 [SMILES: COC(=O)C1(c2cncc(Cl)n2)CCOCC1]

Prepared as for INTC52 using methyl 2-(6-chloropyrazin-2-yl)acetate INTC112 to afford methyl 4-(6-chloropyrazin-2-yl)tetrahydro-2H-pyran-4-carboxylate (12% yield) as a yellow oil. Rt 1.05 min (UPLC, acidic); m/z 257 ($^{35}$Cl M+H)+ (ES+); 1H NMR (500 MHz, DMSO-d6) δ 8.81 (s, 1H), 8.76 (s, 1H), 3.77-3.62 (m, 5H), 3.58-3.49 (m, 2H), 2.38-2.26 (m, 2H), 2.21-2.10 (m, 2H).

Fluorination of Pyrazine Intermediates

Method H: Benzylic Fluorination of Hetero-Aromatic Esters

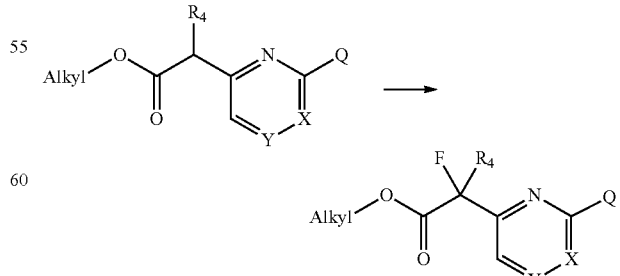

Q = hal e.g. Cl

A solution of hetero-aromatic ester (1 eq) in THF (10 volumes) was cooled to −78° C. to which was added LiHMDS (1.25 eq 1M in THF). The reaction mixture was then warmed to RT for 1 hr. The solution was cooled to −78° C. and a solution (in THF) of, or solid, NSFI (1.25 eq) was added dropwise then warmed to RT for 2 hrs. The solution was diluted with sat. NaHCO$_3$ (aq) and the product was extracted into EtOAc. The crude product was purified by normal phase chromatography.

TABLE 7

The following intermediate was made according to Method H.

| INTC | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| INTC85 | methyl 2-(2-chloropyrimidin-4-yl)-2-fluorobutanoate | Method H using INTC61, [HPLC basic], 233 $^{35}$Cl isotope (1.85). | 8.92 (d, J = 5.1 Hz, 1H), 7.78 (d, J = 5.1 Hz, 1H), 3.75 (s, 3H), 2.45-2.18 (m, 2H), 0.87 (t, J = 7.4 Hz, 3H). |
| INTC124 | methyl 2-(6-chloropyrazin-2-yl)-2-fluorobutanoate | Method H using INTC117, [UPLC basic], no m/z collected (1.22). | 8.91 (s, 1H), 8.90 (s, 1H), 3.76 (s, 3H), 2.48-2.24 (m, 2H), 0.91 (t, J = 7.4 Hz, 3H). |

Amine Intermediate Preparation

Method F: Suzuki Coupling of Heteroaromatic Halides with Aniline Boronates

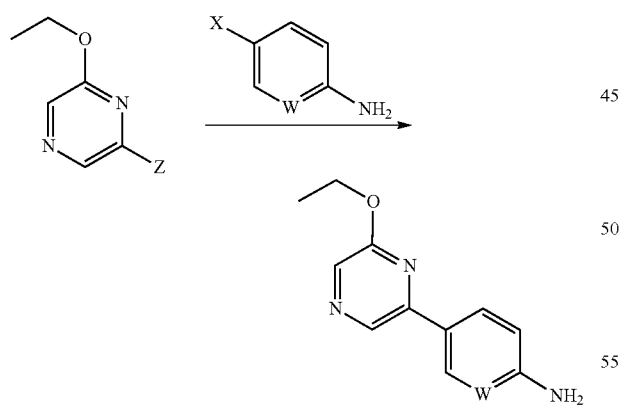

Z = Br, Cl
X = B(OH)$_2$, B(pin)$_2$

Pd catalyst (5 mol %) was added to a degassed (N$_2$, 5 mins) solution of (hetero)aryl-X (1 eq), ethoxypyrazine-Z (1 eq) and base (3 eq, 6.85 mmol) in solvent (3 volumes). The solution was then degassed further (N$_2$, 5 mins) and then heated to 90° C. for 2 hrs then allowed to cool to RT. In general, the desired compound was purified by column chromatography.

Anilines

TABLE 8

The following intermediates were made according to Method F.

| INTC | Name/Structure | Synthesis Method, [LCMS Method], m/z (M + H)+, (Rt/min) | ¹H NMR Chemical Shift Data (DMSO-d6 unless stated) | Catalyst Base, solvent |
|---|---|---|---|---|
| INTD18 | 4-(6-ethoxypyrazin-2-yl)aniline | Method F, [HPLC basic], 216, (1.78). | 8.59 (s, 1H), 8.00 (s, 1H), 7.86-7.75 (m, 2H), 6.69-6.59 (m, 2H), 5.59 (s, 2H), 4.43 (q, J = 7.0 Hz, 2H), 1.38 (t, J = 7.0 Hz, 3H). | Pd(PPh₃)₄, NaHCO₃, MeCN |
| INTD24 | 4-(6-ethoxypyrazin-2-yl)-2-fluoroaniline | Method F, [UPLC basic], 234, (1.31). | 8.66 (s, 1H), 8.06 (s, 1H), 7.84-7.63 (m, 2H), 6.93-6.75 (m, 1H), 5.65 (s, 2H), 4.54-4.34 (m, 2H), 1.47-1.29 (m, 3H). | PdCl₂(dppf), K₂CO₃, dioxane |
| INTD33 | 5-(6-ethoxypyrazin-2-yl)pyridin-2-amine | Method F, [UPLC, basic], 217, (0.98). | 8.70 (dd, J = 2.5, 0.8 Hz, 1H), 8.64 (s, 1H), 8.10-8.06 (m, 2H), 6.54 (dd, J = 8.7, 0.8 Hz, 1H), 6.41 (s, 2H), 4.43 (q, J = 7.0 Hz, 2H), 1.38 (t, J = 7.0 Hz, 3H). | PdCl₂(dppf), Cs₂CO₃, dioxane |

Preparation of Examples

General Methods

Method 2: AlMe₃ Mediated Amide Coupling from Ester

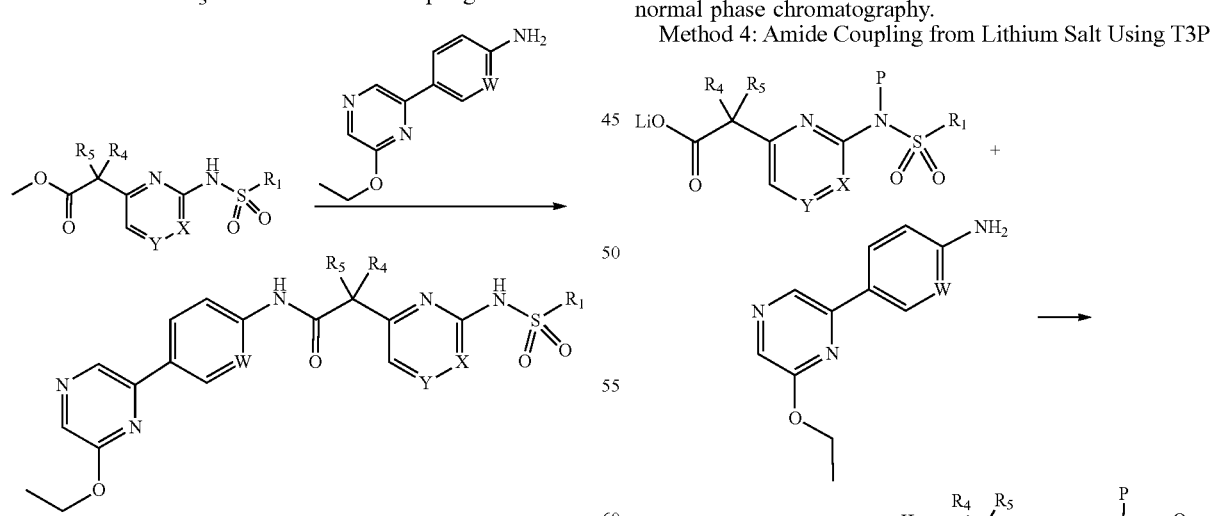

To an ice cooled solution of aniline (2 eq) in toluene (40 volumes) was added AlMe₃ (2.0 M in heptane, 2 eq). The mixture was stirred at this temperature for 5 mins then at RT for 10 mins. To this solution was added ester (1 eq) in one portion and the resultant mixture heated and stirred at 80° C. for 2 hrs. The reaction mixture was cooled in an ice bath and carefully quenched with MeOH (10 volumes). After stirring for 20 mins the mixture was diluted in a mixture of DCM/MeOH (10 volumes), filtered through celite and the filtrate concentrated. The crude product was purified by reverse or normal phase chromatography.

Method 4: Amide Coupling from Lithium Salt Using T3P

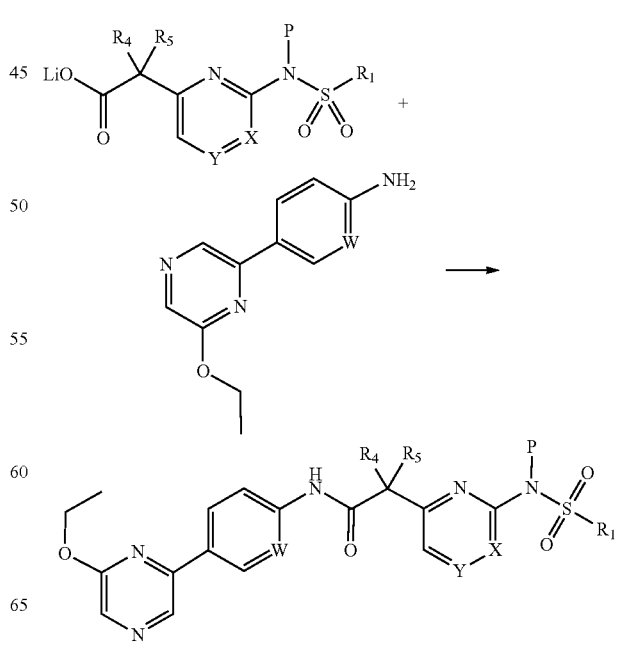

To a solution of lithium salt sulfonamide (1 eq) in DMF (4 volumes) at 0° C. was added aniline (1.2 eq) followed by pyridine (6 eq) and T3P (50 wt % in DMF) (2 eq). The reaction mixture was stirred at 0° C. for 2 hrs then warmed to RT for 20 hrs. The reaction mixture was cooled to 0° C. and further T3P (50 wt % in DMF) (0.6 eq) was added. The reaction mixture was stirred at 0° C. for 1 hr, then RT for 3 hrs. The reaction mixture was diluted with sat. $NH_4Cl$ (aq, 38 volumes) and the resultant precipitate was isolated by filtration, washing with water (2×17 volumes). The resultant yellow precipitate was dissolved in DCM (25 volumes) and MeOH (25 volumes) and concentrated onto silica. The crude product was purified by chromatography on silica gel.

Method 7: Sulfonylation from Aromatic Chloride

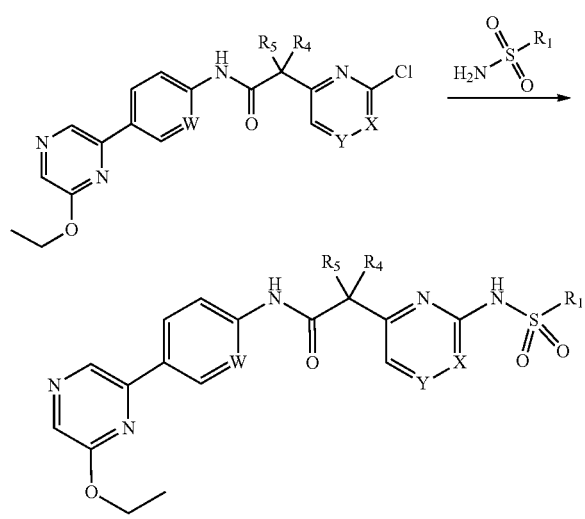

2-Chloro-heteroaromatic intermediate (1 eq), sulfonamide (1.2 eq) and base (2 eq) were dissolved in dioxane (40 volumes). The mixture was degassed (evacuated and backfilled with $N_2$×3) then catalyst (10 mol %) was added. The resulting mixture was heated under nitrogen at 90° C. for 2 hrs. The mixture was cooled to RT, diluted with sat. $NH_4Cl$ (aq, 80 volumes) and DCM (80 volumes). The phases were separated and the aqueous was extracted with further DCM (2×80 volumes). The combined organics were dried ($MgSO_4$), filtered and concentrated in vacuo. The crude product was purified by normal phase chromatography or trituration using a suitable solvent.

Method 10: T3P with Free Acid

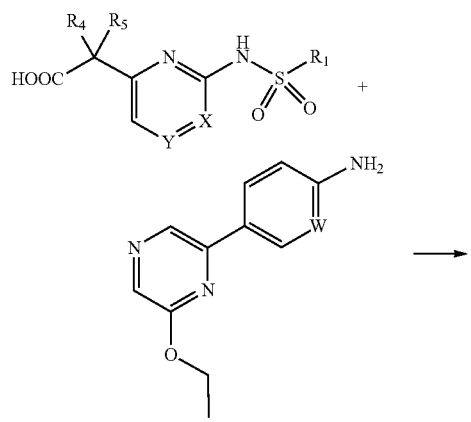

-continued

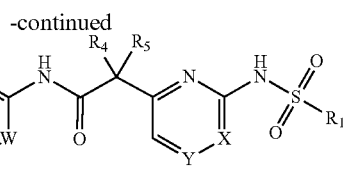

Pyridine (10 eq) followed by T3P (50 wt % in DMF, 2 eq) was added to a stirring solution of amine (1.1 eq) and carboxylic acid (1 eq) in DMF (16 volumes). The resulting reaction was stirred at RT for 24 hrs. The crude reaction mixture was concentrated in vacuo then diluted with $NH_4Cl$ (sat. aq) and extracted with DCM. The combined organic extracts were dried (phase separator) and the solvent removed. The crude product was purified by reverse or normal phase chromatography.

Amide Formation

N-(5-(6-Ethoxypyrazin-2-yl)pyridin-2-yl)-2-fluoro-2-(2-(N-(4-methoxybenzyl)cyclopropanesulfonamido)pyrimidin-4-yl)butanamide INTC51

To a solution of lithium 2-fluoro-2-(2-(N-(4-methoxybenzyl)cyclopropane-sulfonamido)pyrimidin-4-yl)butanoate INTC50 (0.50 g, 1.17 mmol) in DMF (5 mL) at 0° C. was added 5-(6-ethoxypyrazin-2-yl)pyridin-2-amine INTD33 (0.30 g, 1.40 mmol) followed by pyridine (0.57 mL, 7.01 mmol) and T3P (50 wt % in DMF) (1.69 mL, 2.34 mmol). The reaction mixture was stirred at 0° C. for 2 hrs then warmed to RT for 20 hrs. The reaction mixture was cooled to 0° C. and further T3P (50 wt % in DMF) (0.5 mL, 0.69 mmol) was added. The reaction mixture was stirred at 0° C. for 1 hr, then RT for 3 hrs. The reaction mixture was diluted with sat. $NH_4Cl$ (aq, 45 mL) and the resultant precipitate was isolated by filtration, washing with water (2×20 mL). The resultant yellow precipitate was dissolved in DCM (30 mL) and MeOH (30 mL) and concentrated onto silica. The crude product was purified by chromatography on silica gel (24 g column, 0-60% EtOAc/iso-hexane) to afford N-(5-(6-ethoxypyrazin-2-yl)pyridin-2-yl)-2-fluoro-2-(2-(N-(4-methoxybenzyl) cyclopropanesulfonamido)pyrimidin-4-yl) butanamide (0.274 g, 0.433 mmol, 37% yield) as a colourless oil. Rt 1.84 min (UPLC, acidic); m/z 622 (M+H)+ (ES+); $^1$H NMR (500 MHz, DMSO-d6) δ 10.69 (s, 1H), 9.10 (d, J=2.5 Hz, 1H), 8.88-8.81 (m, 2H), 8.52 (dd, J=8.7, 2.5 Hz, 1H), 8.27 (s, 1H), 8.10 (d, J=8.7 Hz, 1H), 7.52 (dd, J=5.2, 1.3 Hz, 1H), 7.30-7.23 (m, 2H), 6.81-6.74 (m, 2H), 5.20-5.08 (m, 2H), 4.48 (q, J=7.0 Hz, 2H), 3.76-3.70 (m, 1H), 3.65 (s, 3H), 2.50-2.39 (m, 1H), 2.38-2.24 (m, 1H), 1.40 (t, J=7.0 Hz, 3H), 1.14-1.06 (m, 1H), 1.10-0.97 (m, 2H), 0.96-0.92 (m, 1H), 0.89 (t, J=7.3 Hz, 3H).

2-(2-(Cyclopropanesulfonamido)pyrimidin-4-yl)-N-(5-(6-ethoxypyrazin-2-yl)pyridin-2-yl)-2-fluorobutanamide P112

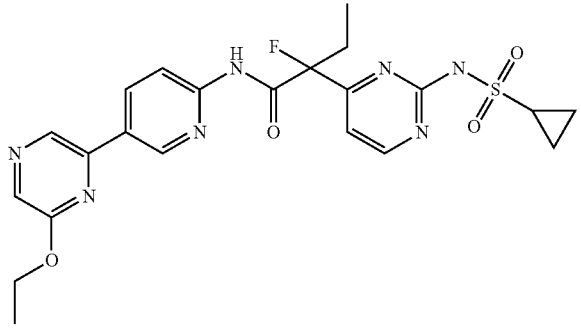 [SMILES: CCOc1cncc(-c2ccc(NC(=O)C(F)(CC)c3ccnc(NS(=O)(=O)C4CC4)n3)nc2)n1]

TFA (0.28 mL, 3.70 mmol) was added into a stirring solution of N-(5-(6-ethoxypyrazin-2-yl)pyridin-2-yl)-2-fluoro-2-(2-(N-(4-methoxybenzyl)cyclopropanesulfonamido)pyrimidin-4-yl)butanamide INTC51 (115 mg, 0.185 mmol) in DCM (10 mL) and the resulting reaction mixture was stirred at RT for 4 hrs. The reaction mixture was concentrated in vacuo and the crude product was purified by chromatography on silica gel (12 g column, 0-100% EtOAc/iso-hexane) to afford 2-(2-(cyclopropanesulfonamido)pyrimidin-4-yl)-N-(5-(6-ethoxypyrazin-2-yl)pyridin-2-yl)-2-fluorobutanamide (77 mg, 0.15 mmol, 81% yield) as a white solid. Rt 2.28 min (HPLC, acidic); m/z 502 (M+H)$^+$ (ES$^+$); $^1$H NMR (500 MHz, DMSO-d6) δ 11.50 (s, 1H), 10.60 (d, J=2.3 Hz, 1H), 9.10 (d, J=2.5 Hz, 1H), 8.87 (s, 1H), 8.76 (d, J=5.1 Hz, 1H), 8.53 (dd, J=8.8, 2.5 Hz, 1H), 8.27 (s, 1H), 8.10 (d, J=8.8 Hz, 1H), 7.48 (d, J=5.1 Hz, 1H), 4.49 (q, J=7.0 Hz, 2H), 3.38-3.27 (m, 1H), 2.44-2.29 (m, 2H), 1.40 (t, J=7.0 Hz, 3H), 1.20-0.92 (m, 7H).

The racemate P112 was separated by chiral preparative HPLC using a Diacel Chiralpak IC column (20% EtOH in [4:1 heptane:chloroform (0.2% TFA):]) to afford P113 and P114.

TABLE 9

Preparation methods and characterisation data of examples

| P | Name/Structure (All examples containing chiral centres are racemates unless stated) | Synthesis Method, [LCMS Method], m/z (M + H)$^+$, (Rt/min) | $^1$H NMR Chemical Shift Data (DMSO-d6 unless stated) |
|---|---|---|---|
| P113 | Single enantiomer - stereochemistry not assigned 2-(2-(Cyclopropanesulfonamido)pyrimidin-4-yl)-N-(5-(6-ethoxypyrazin-2-yl)pyridin-2-yl)-2-fluorobutanamide | P112: [Chiral IC3 HPLC], 10.47, 100% ee at 254 nm; Rt 2.28 mins (HPLC acidic); m/z 502 (M + H)$^+$ (ES$^+$) | 11.50 (s, 1H), 10.60 (d, J = 2.2 Hz, 1H), 9.11 (d, J = 2.4 Hz, 1H), 8.87 (s, 1H), 8.76 (d, J = 5.2 Hz, 1H), 8.53 (dd, J = 8.8, 2.5 Hz, 1H), 8.27 (s, 1H), 8.10 (d, J = 8.8 Hz, 1H), 7.48 (d, J = 5.1 Hz, 1H), 4.49 (q, J = 7.0 Hz, 2H), 3.39-3.26 (m, 1H), 2.54-2.43 (m, 1H), 2.41-2.28 (m, 1H), 1.40 (t, J = 7.0 Hz, 3H), 1.22-0.89 (m, 7H). |
| P114 | Single enantiomer - stereochemistry not assigned 2-(2-(Cyclopropanesulfonamido)pyrimidin-4-yl)-N-(5-(6-ethoxypyrazin-2-yl)pyridin-2-yl)-2-fluorobutanamide | P112: [Chiral IC3 HPLC], 14.24, 100% ee at 254 nm; Rt 2.28 min (HPLC acidic); m/z 502 (M + H)$^+$ (ES$^+$) | 11.50 (s, 1H), 10.60 (d, J = 2.3 Hz, 1H), 9.11 (d, J = 2.4 Hz, 1H), 8.87 (s, 1H), 8.76 (d, J = 5.2 Hz, 1H), 8.53 (dd, J = 8.7, 2.5 Hz, 1H), 8.27 (s, 1H), 8.10 (d, J = 8.7 Hz, 1H), 7.48 (d, J = 5.1 Hz, 1H), 4.49 (q, J = 7.0 Hz, 2H), 3.39-3.25 (m, 1H), 2.55-2.42 (m, 1H), 2.42-2.27 (m, 1H), 1.40 (t, J = 7.0 Hz, 3H), 1.25-0.88 (m, 7H). |
| P115 | 4-(2-(Cyclopropanesulfonamido)pyrimidin-4-yl)-N-(5-(6-ethoxypyrazin-2-yl)pyridin-2-yl)tetrahydro-2H-pyran-4-carboxamide | Method 2 using INTC53 and INTD33, [UPLC, acidic], 528, (1.31) | 11.31 (s, 1H), 10.13 (s, 1H), 9.03 (d, J = 2.5 Hz, 1H), 8.84 (s, 1H), 8.63 (d, J = 5.3 Hz, 1H), 8.50 (dd, J = 8.8, 2.5 Hz, 1H), 8.26 (s, 1H), 8.20 (d, J = 8.8 Hz, 1H), 7.26 (d, J = 5.3 Hz, 1H), 4.48 (q, J = 7.0 Hz, 2H), 3.81-3.69 (m, 2H), 3.67-3.56 (m, 2H), 3.31-3.20 (m, 1H), 2.49-2.41 (m, 2H), 2.25-2.17 (m, 2H), 1.40 (t, J = 7.0 Hz, 3H), 1.09-1.03 (m, 2H), 0.95-0.84 (m, 2H). |

TABLE 9-continued

Preparation methods and characterisation data of examples

| P | Name/Structure (All examples containing chiral centres are racemates unless stated) | Synthesis Method, [LCMS Method], m/z (M + H)+, (Rt/min) | ¹H NMR Chemical Shift Data (DMSO-d6 unless stated) |
|---|---|---|---|
| P136 | 1-(2-(cyclopropanesulfonamido)pyrimidin-4-yl)-N-(5-(6-ethoxy-pyrazin-2-yl)pyridin-2-yl)cyclopentane-1-carboxamide | Method 2 using INTC29 and INTD33, [HPLC acidic], 510, (2.36) | 11.24 (s, 1H), 10.15 (s, 1H), 9.01 (d, J = 2.5 Hz, 1H), 8.84 (s, 1H), 8.60-8.46 (m, 2H), 8.32-8.15 (m, 2H), 7.15 (s, 1H), 4.48 (q, J = 7.0 Hz, 2H), 2.62-2.42 (m, 3H, obscured by DMSO), 2.28-2.13 (m, 2H), 1.80-1.61 (m, 4H), 1.40 (t, J = 7.0 Hz, 3H), 1.09-1.00 (m, 2H), 0.90-0.79 (m, 2H). |
| P137 | 4-(2-(cyclopropanesulfonamido)pyrimidin-4-yl)-N-(4-(6-ethoxy-pyrazin-2-yl)phenyl)tetrahydro-2H-pyran-4-carboxamide | Method 2 using INTC53 and INTD18, [UPLC acidic], 525, (1.38) | 11.33 (s, 1H), 9.54 (s, 1H), 8.76 (s, 1H), 8.64-8.57 (m, 1H), 8.18 (s, 1H), 8.10-8.05 (m, 2H), 7.76 (d, J = 8.6 Hz, 2H), 7.20 (s, 1H), 4.47 (q, J = 7.0 Hz, 2H), 3.78-3.71 (m, 2H), 3.65-3.57 (m, 2H), 3.28-3.22 (m, 1H), 2.45-2.38 (m, 2H), 2.25-2.16 (m, 2H), 1.39 (t, J = 7.0 Hz, 3H), 1.10-1.04 (m, 2H), 0.95-0.88 (m, 2H). |
| P139 | tert-butyl 4-(2-(cyclopropanesulfonamido)pyrimidin-4-yl)-4-((5-(6-ethoxypyrazin-2-yl)pyridin-2-yl)carbamoyl)piperidine-1-carboxylate | Method 2 using INTC77 and INTD33, [UPLC acidic], 625, (1.62) (both Boc-protected and free amine isolated) | 9.00 (d, J = 2.4 Hz, 1H), 8.66 (s, 1H), 8.60 (d, J = 5.3 Hz, 1H), 8.48 (dd, J = 8.7, 2.4 Hz, 1H), 8.39-8.35 (m, 2H), 8.24 (d, J = 8.7 Hz, 1H), 8.14 (s, 1H), 7.24 (d, J = 5.3 Hz, 1H), 4.54 (q, J = 7.0 Hz, 2H), 3.77-3.70 (m, 2H), 3.48-3.44 (m, 2H), 3.32-3.26 (m, 1H), 2.56-2.50 (m, 2H), 2.31-2.23 (m, 2H), 1.51-1.43 (m, 12H), 1.33-1.21 (m, 2H), 1.07-0.99 (m, 2H). |
| P143 | 4-(2-(cyclopropanesulfonamido)pyrimidin-4-yl)-N-(4-(6-ethoxy-pyrazin-2-yl)-2-fluorophenyl)tetrahydro-2H-pyran-4-carboxamide | Method 2 using INTC53 and INTD24, [UPLC acidic], 543, (1.37) | 11.33 (s, 1H), 9.47 (s, 1H), 8.84 (s, 1H), 8.63 (d, J = 5.3 Hz, 1H), 8.25 (s, 1H), 8.03-7.93 (m, 2H), 7.64-7.57 (m, 1H), 7.22 (d, J = 5.3 Hz, 1H), 4.48 (q, J = 7.0 Hz, 2H), 3.79-3.71 (m, 2H), 3.67-3.59 (m, 2H), 3.31-3.27 (m, 1H), 2.44-2.37 (m, 2H), 2.24-2.15 (m, 2H), 1.39 (t, J = 7.0 Hz, 3H), 1.15-1.08 (m, 2H), 1.05-0.98 (m, 2H). |

TABLE 9-continued

Preparation methods and characterisation data of examples

| P | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| P145 | 2-(2-(cyclopropanesulfonamido)pyrimidin-4-yl)-N-(5-(6-ethoxy-pyrazin-2-yl)pyridin-2-yl)-4-methoxybutanamide | Method 7 using INTC89, [UPLC acidic], 514, (1.3) | 11.24 (s, 1H), 11.03 (s, 1H), 9.06 (d, J = 2.4 Hz, 1H), 8.84 (s, 1H), 8.56 (d, J = 5.2 Hz, 1H), 8.49 (dd, J = 8.7, 2.4 Hz, 1H), 8.25 (s, 1H), 8.19 (d, J = 8.7 Hz, 1H), 7.21 (d, J = 5.2 Hz, 1H), 4.48 (q, J = 7.0 Hz, 2H), 4.22 (dd, J = 8.4, 6.1 Hz, 1H), 3.41-3.32 (m, 3H), 3.21 (s, 3H), 2.36-2.25 (m, 1H), 2.20-2.06 (m, 1H), 1.40 (t, J = 7.0 Hz, 3H), 1.16-1.03 (m, 2H), 1.02-0.89 (m, 2H). |
| P165 | Single enantiomer - stereochemistry unassigned N-(5-(6-ethoxy-pyrazin-2-yl)pyridin-2-yl)-2-fluoro-2-(2-(methylsulfonamido)-pyrimidin-4-yl)butanamide | Method 2 using INTC74 and INTD33, Chiral IC6 (14.67), [UPLC acidic], 476, (1.36) | 11.55 (s, 1H), 10.60 (s, 1H), 9.10 (d, J = 2.4 Hz, 1H), 8.85 (s, 1H), 8.76-8.71 (m, 1H), 8.52 (dd, J = 8.7, 2.4 Hz, 1H), 8.26 (s, 1H), 8.10 (d, J = 8.7 Hz, 1H), 7.47-7.43 (m, 1H), 4.47 (q, J = 7.0 Hz, 2H), 3.39 (s, 3H), 2.48-2.29 (m, 2H), 1.39 (t, J = 7.0 Hz, 3H), 0.92 (t, J = 7.3 Hz, 3H). |
| P166 | Single enantiomer - stereochemistry unassigned N-(5-(6-ethoxy-pyrazin-2-yl)pyridin-2-yl)-2-fluoro-2-(2-(methylsulfonamido)-pyrimidin-4-yl)butanamide | Method 2 using INTC74 and INTD33, Chiral IC6 (17.03), [UPLC acidic], 476, (1.36) | 11.56 (s, 1H), 10.62 (s, 1H), 9.11 (d, J = 2.4 Hz, 1H), 8.87 (s, 1H), 8.77-8.72 (m, 1H), 8.53 (dd, J = 8.7, 2.4 Hz, 1H), 8.27 (s, 1H), 8.11 (d, J = 8.7 Hz, 1H), 7.46-7.42 (m, 1H), 4.49 (q, J = 7.0 Hz, 2H), 3.38 (s, 3H), 2.44-2.27 (m, 2H), 1.40 (t, J = 7.0 Hz, 3H), 0.93 (t, J = 7.3 Hz, 3H). |
| P186 | 4-(6-(cyclopropanesulfonamido)pyridin-2-yl)-N-(5-(6-ethoxypyrazin-2-yl)pyridin-2-yl)tetrahydro-2H-pyran-4-carboxamide | Method 2 using INTC108 and INTD33, [HPLC acidic], 525, (2.23) | 10.62 (s, 1H), 9.75 (s, 1H), 9.00 (d, J = 2.4 Hz, 1H), 8.83 (s, 1H), 8.49 (dd, J = 8.8, 2.4 Hz, 1H), 8.25 (s, 1H), 8.17 (d, J = 8.8 Hz, 1H), 7.79-7.76 (m, 1H), 7.19 (d, J = 7.7 Hz, 1H), 6.85 (d, J = 8.1 Hz, 1H), 4.47 (q, J = 7.1 Hz, 2H), 3.74-3.60 (m, 4H), 3.24-3.16 (m, 1H), 2.53-2.46 (m, 2H, obscured by DMSO), 2.27-2.19 (m, 2H), 1.40 (t, J = 7.1 Hz, 3H), 1.06-1.01 (m, 2H), 0.94-0.84 (m, 2H). |

TABLE 9-continued

Preparation methods and characterisation data of examples

| P | Name/Structure (All examples containing chiral centres are racemates unless stated) | Synthesis Method, [LCMS Method], m/z (M + H)+, (Rt/min) | $^1$H NMR Chemical Shift Data (DMSO-d6 unless stated) |
|---|---|---|---|
| P197 | 4-(6-(cyclopropanesulfonamido)pyrazin-2-yl)-N-(5-(6-ethoxypyrazin-2-yl)pyridin-2-yl)tetrahydro-2H-pyran-4-carboxamide | Method 2 using INTC127 and INTD33, [UPLC acidic], 526, (1.31) | 11.06 (s, 1H), 10.14 (s, 1H), 9.01 (d, J = 2.5 Hz, 1H), 8.84 (s, 1H), 8.49 (dd, J = 8.7, 2.5 Hz, 1H), 8.45 (s, 1H), 8.25 (s, 1H), 8.22-8.16 (m, 2H), 4.47 (q, J = 7.0 Hz, 2H), 3.79-3.72 (m, 2H), 3.68-3.60 (m, 2H), 3.15-3.05 (m, 1H), 2.56-2.52 (m, 2H), 2.27-2.17 (m, 2H), 1.39 (t, J = 7.0 Hz, 3H), 1.08-1.02 (m, 2H), 0.88-0.80 (m, 2H). |
| P206 | Single enantiomer - stereochemistry unassigned 2-(6-(cyclopropane-sulfonamido)pyrazin-2-yl)-N-(5-(6-ethoxypyrazin-2-yl)pyridin-2-yl)-2-fluorobutanamide | Method 10 using INTC133 and INTD33, Chiral IC5 (12.55), [HPLC acidic], 502, (2.27) | 11.25 (s, 1H), 10.61 (d, J = 2.4 Hz, 1H), 9.10 (d, J = 2.4 Hz, 1H), 8.87 (s, 1H), 8.64 (s, 1H), 8.53 (dd, J = 8.7, 2.4 Hz, 1H), 8.34 (s, 1H), 8.27 (s, 1H), 8.12 (d, J = 8.7 Hz, 1H), 4.49 (q, J = 7.0 Hz, 2H), 3.19-3.10 (m, 1H), 2.58-2.34 (m, 2H), 1.40 (t, J = 7.1 Hz, 3H), 1.23-0.91 (m, 7H). |
| P207 | Single enantiomer - stereochemistry unassigned 2-(6-(cyclopropane-sulfonamido)pyrazin-2-yl)-N-(5-(6-ethoxypyrazin-2-yl)pyridin-2-yl)-2-fluorobutanamide | Method 10 using INTC133 and INTD33, Chiral IC5 (19.98), [HPLC acidic], 502, (2.27) | 11.25 (s, 1H), 10.61 (d, J = 2.4 Hz, 1H), 9.10 (d, J = 2.4 Hz, 1H), 8.87 (s, 1H), 8.64 (s, 1H), 8.53 (dd, J = 8.7, 2.4 Hz, 1H), 8.33 (s, 1H), 8.27 (s, 1H), 8.12 (d, J = 8.7 Hz, 1H), 4.49 (q, J = 7.1 Hz, 2H), 3.19-3.10 (m, 1H), 2.58-2.34 (m, 2H), 1.40 (t, J = 7.0 Hz, 3H), 1.20-0.90 (m, 7H). |

Biological Examples

Biological Example 1—Human CTPS1 Enzyme Inhibition

The enzyme inhibitory activities of compounds invented against the target of interest were determined using the ADP-Glo™ Max assay (Promega, UK). Assays for human CTPS1 were performed in 1× assay buffer containing 50 mM Tris, 10 mM MgCl$_2$, 0.01% Tween-20, pH to 8.0 accordingly. Finally, immediately before use, L-cysteine was added to the 1× assay buffer to a final concentration of 2 mM. All reagents are from Sigma-Aldrich unless specified otherwise. Human full length active C-terminal FLAG-Hiss-tag CTPS1 (UniProtKB—P17812, CTPS[1-591]-GGDYKDDDDKGGHHHHHHHH) was obtained from Proteros biostructures GmbH.

Assay Procedure

3× human CTPS1 protein was prepared in 1× assay buffer to the final working protein concentration required for the reaction. A 2 uL volume per well of 3× human CTPS1 protein was mixed with 2 uL per well of 3× test compound (compound prepared in 1× assay buffer to an appropriate final 3× compound concentration respective to the concentration response curve designed for the compounds under test) for 10 minutes at 25° C. The enzymatic reaction was then initiated by addition of a 2 uL per well volume of a pre-mixed substrate mix (UltraPure ATP from ADP-Glo™ Max kit (0.31 mM), GTP (0.034 mM), UTP (0.48 mM) and L-glutamine (0.186 mM)) and the mixture was incubated for an appropriate amount of time within the determined linear phase of the reaction at 25° C. under sealed plate conditions with constant agitation at 500 revolutions per minute (rpm). ADP-Glo™ Max reagent was added for 60 minutes (6 μL per well) and subsequently ADP-Glo™ Max development reagent was added for 60 minutes (12 uL per well) prior to signal detection in a microplate reader (EnVision® Multi-label Reader, Perkin Elmer). Following each reagent addition over the course of the assay, assay plates were pulse centrifuged for 30 seconds at 500 rpm.

In all cases, the enzyme converts ATP to ADP and the ADP-Glo™ Max reagent subsequently depletes any remaining endogenous ATP in the reaction system. The ADP-Glo™ Max detection reagent converts the ADP that has been enzymatically produced back into ATP and using ATP as a substrate together with luciferin for the enzyme luciferase, light is generated which produces a detectable luminescence. The luminescent signal measured is directly proportional to the amount of ADP produced by the enzyme reaction and a reduction in this signal upon compound treatment demonstrates enzyme inhibition. The percentage inhibition produced by each concentration of compound was calculated using the equation shown below:

$$\% \text{ Inhibition} = 1 - \frac{(Mean_{Min} - Mean_{Inh})}{(Mean_{Min} - Mean_{Max})} \times 100$$

Percentage inhibition was then plotted against compound concentration, and the 50% inhibitory concentration ($IC_{50}$) was determined from the resultant concentration-response curve.

The data for all compounds of formula (I) tested are presented below.

TABLE 10

Human CTPS1 Enzyme Inhibition data grouped by potency range (++ indicates $IC_{50}$ in the range >0.1 to 1 micromolar, +++ indicates $IC_{50}$ of ≤0.1 micromolar)

| P | CTPS1 |
|---|---|
| P113 | +++ |
| P114 | +++ |
| P115 | +++ |
| P136 | +++ |
| P137 | +++ |
| P139 | ++ |
| P143 | +++ |
| P145 | +++ |
| P165 | +++ |
| P166 | +++ |
| P186 | +++ |
| P197 | +++ |
| P206 | +++ |
| P207 | +++ |

All compounds of the invention which have been tested were found to demonstrate inhibition of CTPS1 enzyme in this assay. Consequently, these compounds may be expected to have utility in the inhibition of CTPS1. The compounds of the invention are also expected to have utility as research tools, for example, for use in CTPS assays.

Biological Example 2—RapidFire/MS-based Enzyme Selectivity Assays

Human CTPS1 Versus CTPS2 Selectivity Assessment by RapidFire/MS Analysis.

The enzyme inhibitory activities against each target isoform of interest may be determined for the compounds of the invention using an optimised RapidFire high-throughput mass spectrometry (RF/MS) assay format. RF/MS assays for both human CTPS1 and CTPS2 may be performed in assay buffer consisting of 50 mM HEPES (Merck), 20 mM $MgCl_2$, 5 mM KCl, 1 mM DTT, 0.01% Tween-20, pH to 8.0 accordingly. Human full-length active C-terminal FLAG-His-tag CTPS1 (UniProtKB—P17812, CTPS[1-591]-GGDYKDDDDKGGHHHHHHHH) may be obtained from Proteros biostructures GmbH. Human full length active C-terminal FLAG-His-Avi tagged CTPS2 (UniProtKB—Q9NRF8, CTPS2 [1-586]-DYKDDDDKHHHHHHGLN-DIFEAQKIEWHE) may be obtained from Harker Bio.

Assay Procedure

Human CTPS (1 or 2) protein may be prepared in 1× assay buffer to the final working protein concentration required for the reaction. A 2 uL volume per well of 2×CTPS (1 or 2) protein may be mixed with 40 nL of compound using acoustic (ECHO) delivery and incubated for 10 minutes at 25° C. Each isoform enzymatic reaction may be subsequently initiated by addition of 2 uL per well of a 2× substrate mix in assay buffer. For hCTPS1: ATP (0.3 mM), UTP (0.2 mM), GTP (0.07 mM) and L-glutamine (0.1 mM). For hCTPS2: ATP (0.1 mM), UTP (0.04 mM), GTP (0.03 mM) and L-glutamine (0.1 mM). Each mixture may be incubated for an appropriate amount of time per isoform within the determined linear phase of the reaction at 25° C. A 60 uL volume of stop solution (1% formic acid with 0.5 uM $^{13}C_9$-$^{15}$N3-CTP in $H_2O$) may be added and the plate immediately heat-sealed and centrifuged for 10 minutes at 4,000 rpm. Following centrifugation, plates may be loaded onto the Agilent RapidFire microfluidic solid phase extraction system coupled to an AP14000 triple quadrupole mass spectrometer (RF/MS) for analysis.

In all cases, the enzyme converts UTP to CTP. Highly specific and sensitive multiple reaction monitoring (MRM) MS methods may be optimised for the detection of the enzymatic reaction product, CTP, and the stable isotope labelled product standard $^{13}C_9$-$^{15}N_3$-CTP. Readout for data analysis may be calculated as the ratio between the peak area of the product CTP and the internal standard $^{13}C_9$-$^{15}N_3$-CTP. For data reporting, the following equation may be used:

$$R = \frac{P}{IS}$$

(R=ratio/readout, P=product signal area, IS=internal standard signal area)

For each screening plate, the means of the negative (DMSO) and positive control values were used for the calculation of the respective assay window (S/B) and Z' values. The median of the respective control values was used for calculation of percent inhibition according to the following equation:

$$I = \frac{R_{neg} - R_{sample}}{[R_{neg} - R_{pos}]} \%$$

(I=Inhibition, $R_{neg}$=median of negative control readout values, $R_{pos}$=median of positive control readout values, $R_{sample}$=sample readout value)

Percentage inhibition was then plotted against compound concentration, and the 50% inhibitory concentration ($IC_{51}$) was determined from the resultant concentration-response curve.

Fold selectivity between CTPS1 and CTPS2 was subsequently calculated according to the following equation:

$$\text{Fold selectivity} = \frac{CTPS2 \ IC_{50}}{CTPS1 \ IC_{50}}$$

Certain compounds of formula (I) were tested in the assay above. The data for all compounds tested are presented below.

TABLE 11

| P | Selectivity |
|---|---|
| P113 | + |
| P114 | +++ |
| P115 | +++ |
| P136 | +++ |
| P143 | +++ |
| P145 | +++ |
| P197 | +++ |
| P206 | +++ |
| P207 | + |

Selectivity data split into grouping of 2-30 fold (+) or >60 fold (+++)

All compounds tested in the assay described in Biological Example 2 were found to have at least 2 fold selectivity for CTPS1 over CTPS2, with many compounds having a selectivity for CTPS1 of over 60 fold. In particular, these compounds may be expected to have utility in the treatment of diseases whereby a selective CTPS1 compound is beneficial.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

REFERENCES

Evans, D. R. & Guy, H. I. Mammalian pyrimidine biosynthesis: fresh insights into an ancient pathway. J. Biol. Chem. 279, 33035-33038 (2004).

Fairbanks, L. D. et al. Importance of ribonucleotide availability to proliferating T-lymphocytes from healthy humans. Disproportionate expansion of pyrimidine pools and contrasting effects of de novo synthesis inhibitors. J. Biol. Chem. 270, 29682-29689 (1995).

Higgins, M. J. et al. Regulation of human cytidine triphosphate synthetase 1 by glycogen synthase kinase 3. J. Biol. Chem. 282, 29493-29503 (2007).

Kursula, P. et al. Structure of the synthetase domain of human CTP synthetase, a target for anticancer therapy. Acta Crystallogr Sect F Struct Biol Cryst Commun. 62 (Pt7): 613-617 (2006).

Lieberman I. Enzymatic amination of uridine triphosphate to cytidine triphosphate. The J. Biol. Chem. 222 (2): 765-75 (1956).

Martin E. et al. CTP synthase 1 deficiency in humans reveals its central role in lymphocytes proliferation. Nature. June 12; 510(7504):288-92 (2014). Erratum in: Nature. July 17; 511(7509):370 (2014).

McCluskey G D et al., Exploring the Potent Inhibition of CTP Synthase by Gemcitabine-5'-Triphosphate. Chembiochem. 17, 2240-2249 (2016).

Ostrander, D. B. et al. Effect of CTP synthetase regulation by CTP on phospholipid synthesis in *Saccharomyces cerevisiae*. J. Biol. Chem. 273, 18992-19001 (1998).

Sakamoto K. et al. Identification of cytidine-5-triphosphate synthase1-selective inhibitory peptide from random peptide library displayed on T7 phage. Peptides. 2017; 94:56-63 (2017).

Salu et al. Drug-eluting stents: a new treatment in the prevention of restenosis Part I: experimental studies. Acta Cardiol, 59, 51-61 (2004).

Sousa J. E. et al. Drug-Eluting Stents. Circulation, 107 (2003) 2274 (Part I), 2283 (Part II).

Tang R. et al. CTP synthase 1, a smooth muscle-sensitive therapeutic target for effective vascular repair. Arterioscler Thromb Vasc Biol. 33(10), 1-19, (2013).

van den Berg, A. A. et al. Cytidine triphosphate (CTP) synthetase activity during cell cycle progression in normal and malignant T-lymphocytic cells. Eur. J. Cancer 31, 108-112 (1995).

van Kuilenburg, A. B. P. et al. Identification of a cDNA encoding an isoform of human CTP synthetase. Biochimica et Biophysica Acta 1492548-552 (2000).

The invention claimed is:

1. A compound which is 4-(2-(cyclopropanesulfonamido)pyrimidin-4-yl)-N-(5-(6-ethoxypyrazin-2-yl)pyridin-2-yl)tetrahydro-2H-pyran-4-carboxamide:

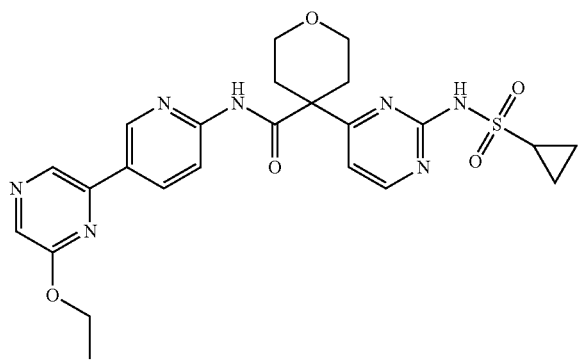 [SMILES: CCOc1cncc(-c2ccc(NC(=O)C3(c4ccnc(NS(=O)(=O)C5CC5)n4)CCOCC3)nc2)n1]

or a salt and/or solvate thereof.

2. The salt according to claim 1 wherein the salt is a pharmaceutically acceptable salt of 4-(2-(cyclopropanesulfonamido)pyrimidin-4-yl)-N-(5-(6-ethoxypyrazin-2-yl)pyridin-2-yl)tetrahydro-2H-pyran-4-carboxamide:

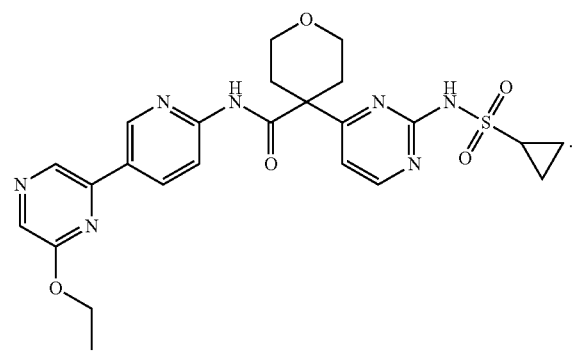 [SMILES: CCOc1cncc(-c2ccc(NC(=O)C3(c4ccnc(NS(=O)(=O)C5CC5)n4)CCOCC3)nc2)n1]

3. The compound according to claim 1 wherein the compound is 4-(2-(cyclopropanesulfonamido)pyrimidin-4-yl)-N-(5-(6-ethoxypyrazin-2-yl)pyridin-2-yl)tetrahydro-2H-pyran-4-carboxamide:
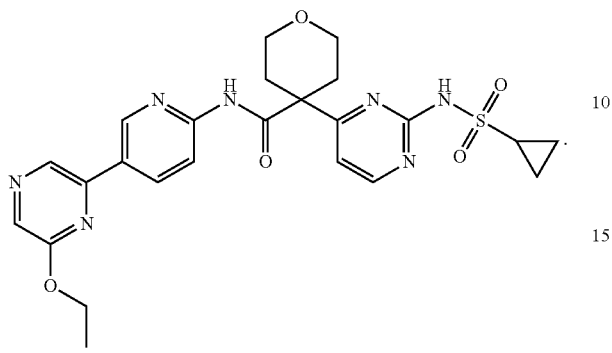
4. A pharmaceutical composition comprising the compound according to claim 3.
5. A pharmaceutical composition comprising the pharmaceutically acceptable salt according to claim 2.
* * * * *